US008415030B2

(12) United States Patent
Chi et al.

(10) Patent No.: US 8,415,030 B2
(45) Date of Patent: Apr. 9, 2013

(54) PHOSPHORESCENT TRANSITION METAL COMPLEX HAVING A FACIALLY ARRANGED CARBON-PHOSPHORUS-CARBON (C^P^C) TRIDENTATE CHELATE AND ORGANIC LIGHT EMITTING DIODE CONTAINING THE SAME

(75) Inventors: Yun Chi, Hsinchu (TW); Jui-Yi Hung, Hsinchu (TW); Pi-Tai Chou, Taipei (TW); Cheng-Huei Lin, Hsinchu (TW)

(73) Assignee: National Tsing Hua University (TW)

( * ) Notice: Subject to any disclaimer, the term of this patent is extended or adjusted under 35 U.S.C. 154(b) by 496 days.

(21) Appl. No.: 12/656,927

(22) Filed: Feb. 19, 2010

(65) Prior Publication Data

US 2011/0204770 A1    Aug. 25, 2011

(51) Int. Cl.
 *H01L 51/54* (2006.01)
 *C09K 11/06* (2006.01)
(52) U.S. Cl.
 USPC .......... 428/690; 428/917; 548/103; 546/4; 556/13; 313/504; 313/506; 252/301.16; 257/40; 257/E51.044

(58) Field of Classification Search ................ None
See application file for complete search history.

(56) References Cited

U.S. PATENT DOCUMENTS

2002/0048689 A1*  4/2002  Igarashi et al. ............. 428/690

OTHER PUBLICATIONS

Nolte et al. "Crystal and molecular structure of [IrP{(OC6H3Me)2(OC6H4Me)}Cl(y-picoline)2] formed by the ortho-cyclometallation of two ortho-tolyl groups on a single tri-ortho-tolylphosphite ligand". Journal of Organometallic Chemistry. 1977, vol. 142, No. 3, pp. 387-395.*

* cited by examiner

*Primary Examiner* — Michael H Wilson
(74) *Attorney, Agent, or Firm* — Bacon & Thomas, PLLC

(57) ABSTRACT

The present invention provides a series of phosphorescent transition metal complexes having a facially arranged, carbon-phosphorus-carbon (C^P^C) tridentate chelate, alone with one monoanionic bidentate chromophoric chelate (either C^N or A^N) and one arbitrary charge neutral chelate (L), or with one charge neutral bidentate chromophoric chelate (N^N) and one arbitrary anionic ligand (X); all of them can be used to generate high efficiency photo-induced phosphorescence at room temperature, as well as bright electroluminescence upon employment of these materials in the fabrication of organic light-emitting devices.

27 Claims, 11 Drawing Sheets

PHOSPHORESCENT TRANSITION METAL COMPLEX HAVING A FACIALLY ARRANGED CARBON-PHOSPHORUS-CARBON (C^P^C) TRIDENTATE CHELATE AND ORGANIC LIGHT EMITTING DIODE CONTAINING THE SAME

FIELD OF THE INVENTION

The present invention relates to a transition-metal based, highly efficient luminescent material, and more particularly to a phosphorescent iridium complex with a facially arranged tridentate carbon-phosphorus-carbon (C^P^C) chelate, a synthetic method thereof and a phosphorescent organic light emitting diode containing the same.

BACKGROUND OF THE INVENTION

Phosphorescent organic light emitting diodes (OLEDs) are under intensive investigation because of their potential of achieving improved device brightness and performances. In contrast to the fluorescent emission, the electrophosphorescence of heavy transition-metal complexes are easily generated from both singlet and triplet excited states and, thus, the internal quantum efficiency can reach a theoretical level of unity, rather than the 25% inherent upper limit imposed by the formation of singlet excitons for the respective fluorescent counterparts. Thus, a great deal of effort has been spent on the second and third-row transition metal complexes, for developing highly efficient phosphors that can emit all three primary colors.

US 2008-0161568 A1 discloses the phosphorescent tris-chelated transition metal complexes comprising i) two identical non-conjugated cyclometalated ligands being incorporated into a coordination sphere thereof with a transition metal, and one chelating chromophore (or chromophoric chelate) being incorporated into the coordination sphere; or ii) one non-conjugated cyclometalated ligand forming a coordination sphere thereof with a transition metal, and two chelating chromophores being incorporated into the coordination sphere, wherein the metal is iridium, platinum, osmium or ruthenium. The chelating chromophore possesses a relatively lower energy gap in comparison with that of the non-conjugated cyclometalated ligand, the latter afforded an effective barrier for inhibiting the ligand-to-ligand charge transfer process, so that a subsequent radiative decay from an excited state of these transition complexes will be confined to the chelating chromophore. The architecture and energy gap of the chelating chromophore are suitable for generation of high efficiency blue, green and even red emissions.

US 2009-0209756 A1 discloses a phosphorescent tris-chelated transition metal complex comprising i) two identical carbon-nitrogen (C^N) or azolate-nitrogen (A^N) chromophoric chelates being incorporated into a coordination sphere thereof with a transition metal, and one carbon-phosphorus (C^P) chelate being incorporated into the coordination sphere; or ii) one carbon-nitrogen (C^N) or azolate-nitrogen (A^N) chromophoric chelate forming a coordination sphere thereof with a transition metal, and two identical carbon-phosphorus (C^P) chelates being incorporated into the coordination sphere, wherein the metal is iridium, platinum, osmium or ruthenium. The chromophoric chelates possess a relatively lower energy gap in comparison with that of the non-chromophoric chelate, the latter afforded an effective barrier for inhibiting the ligand-to-ligand charge transfer process, so that bright phosphorescence can be observed. The architecture and energy gap of this molecular design are suitable for generation of high efficiency blue, green and even red emissions. The disclosures of US 2008-0161568 A1 and US 2009-0209756 A1 are incorporated herein by reference.

However, these published patent applications do not propose a transition metal complex with carbon-phosphorus-carbon (C^P^C) tridentate chelate, i.e. facially arranged, di-cyclometalated phosphinite chelate.

SUMMARY OF THE INVENTION

A primary objective of the present invention is to provide a phosphorescent transition metal complex for use as an electrophosphorescent material in a light emitting layer of an organic electroluminescent device. This complex may also be used as a catalyst.

Another objective of the present invention is to provide a transition metal complex for use as an electrophosphorescent material in a light emitting layer of an electroluminescent device capable of emitting blue light.

The phosphorescent transition metal complex according to the present invention is a transition metal complex with carbon-phosphorus-carbon (C^P^C) tridentate chelate, i.e. facially arranged, di-cyclometalated phosphinite chelate. Their generalized structures are represented by the following structural drawings Ia, Ib, Ic, or their stereo isomers, which comprises one facially arranged, carbon-phosphorus-carbon (C^P^C) tridentate chelate, and one bidentate carbon-nitrogen (C^N) or azolate-nitrogen (A^N) anionic chromophoric chelate, together with one arbitrary neutral donor ligand (L), as shown in Ia or Ib; or comprises one facially arranged, carbon-phosphorus-carbon (C^P^C) tridentate chelate, and one neutral diimine nitrogen-nitrogen (N^N) chromophoric chelate, together with one arbitrary anionic donor ligand (X), as shown in Ic:

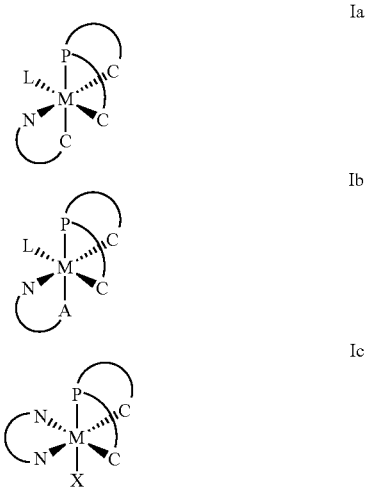

wherein M is the transition metal and is iridium, osmium or ruthenium;

the carbon atom (C) and nitrogen atom (N) linked with an arch (C^N), azolic nitrogen atom (A) and nitrogen atom (N) linked with an arch (A^N), or neutral diimine ligand with two nitrogen atoms (N^N) have a general representation of $Ar^1$-$Ar^2$, wherein $Ar^1$ is aryl, substituted aryl or polyaromatic fragment in the C^N chelate of Ia; pyrrolide, functionalized pyrrolide, pyrazolate, functionalized pyrazolate, triazolate, functionalized triazolate or tetrazolate group in the A^N chelate of Ib; or heterocyclic nitrogen donor group in the diimine N^N chelate of Ic, while Ar² in each of the C^N, A^N and N^N chelates of formula Ia, Ib and Ic is a neutral heteroaromatic N-containing donor group; and the carbon atom (C) and phosphorous atom (P) and carbon atom (C) linked with two arches (C^P^C) have a formula of PR⁴(OAr⁵)₂, wherein R⁴ is alkyl, aryl, substituted aryl, aryloxyl, or substituted aryloxyl; and Ar⁵ is an aryl or substituted aryl comprising a R⁵ substituent, wherein R⁵ is alkyl, alkoxyl, halide, or pseduohalide; and the two carbon atoms in the C^P^C of the formulas represent the ortho-cyclometalated carbon atoms of the aryl rings, Ar⁵.

Preferably, M is iridium, and Ar⁵ is phenyl or substituted phenyl.

Preferably, the complex is presented by the formulas Ia or Ib, wherein L in formula Ia and Ib is a phosphorous donor ligand PR¹R²R³, and R¹, R², and R³ independently are alkyl, alkoxyl, aryl, substituted aryl, aryloxyl or substituted aryloxyl. More preferably, R¹, R², and R³ independently are methyl, phenyl, or phenoxyl.

Preferably, the complex is presented by the formulas Ia or Ib, wherein L in formula Ia and Ib is a non-phosphorous donor ligand such as AsR¹R²R³, wherein R¹, R², and R³ independently are alkyl, alkoxyl, aryl, substituted aryl, aryloxyl or substituted aryloxyl; or an arbitrary nitrogen donor ligand such as pyridine or functionalized pyridine.

Preferably, the complex is presented by the formula Ic, wherein X in formula Ic is an inorganic anion selected from the group consisting of acetate, halide, cyanide, isocyanate, thiocyanate, and pseudohalide; or an organic anion selected from the group consisting of aryl, alkoxyl, phenoxide, substituted phenoxide, azolate, thiolate, functionalized azolate, acetylide, and substituted acetylide.

Preferably, R⁴ is methoxyl, phenoxyl, or phenyl. More preferably, R⁴ is phenoxyl.

Preferably, the carbon-nitrogen (C^N) chelate is

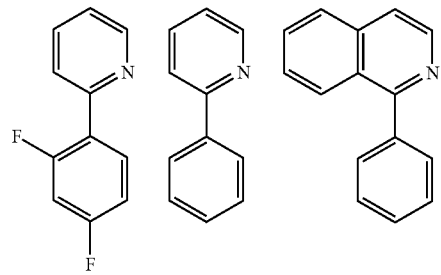

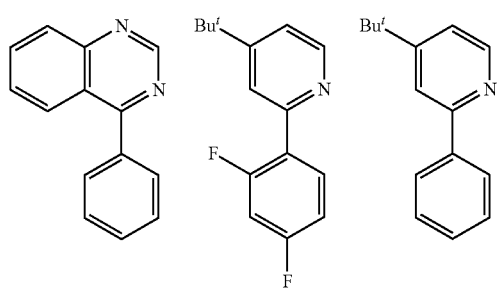

-continued

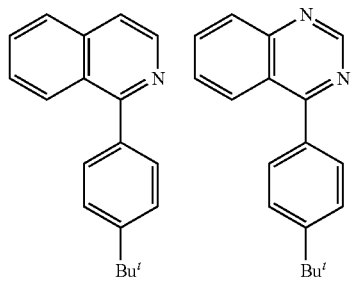

wherein Bu^t is tert-butyl.

Preferably, the azolate-nitrogen (A^N) chelate is

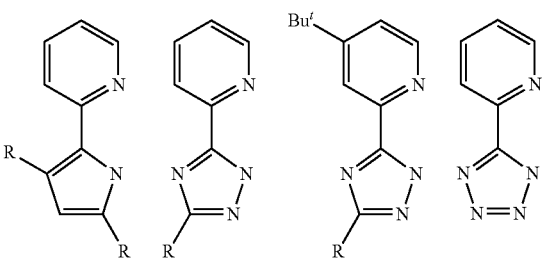

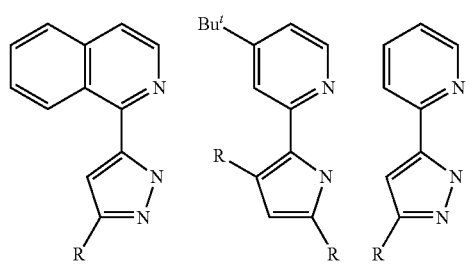

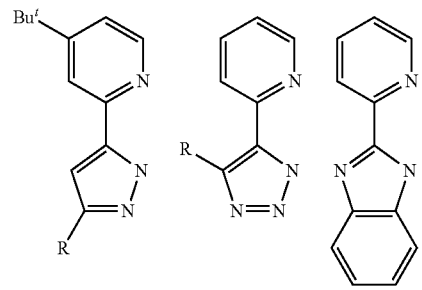

wherein R is hydrogen, CF₃, methyl, tert-butyl, small alkyl, phenyl or substituted phenyl group, and Bu^t is tert-butyl.

Preferably, the diimine nitrogen-nitrogen (N^N) chelate is

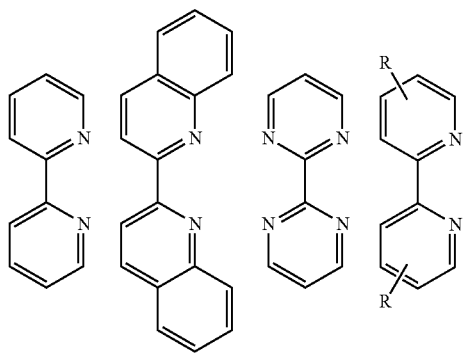

wherein R is hydrogen, methyl, tert-butyl, small alkyl, phenyl, substituted aryl, fluoride, halide, pseudohalide, methoxyl, dimethylamino, or diphenylamino.

Preferably, the diimine nitrogen-nitrogen (N^N) chelate is

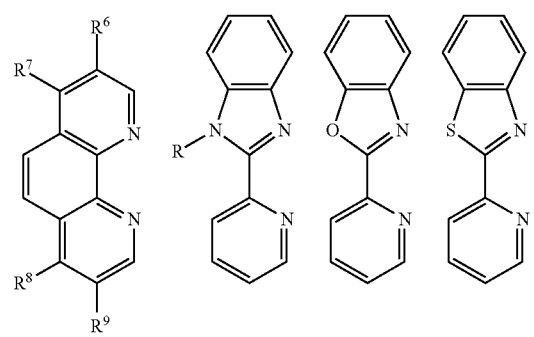

wherein R, $R^6$, $R^7$, $R^5$, and $R^9$ independently are hydrogen, methyl, ethyl, small alkyl, phenyl, or substituted phenyl.

Preferably, the complex is represented by the following formula:

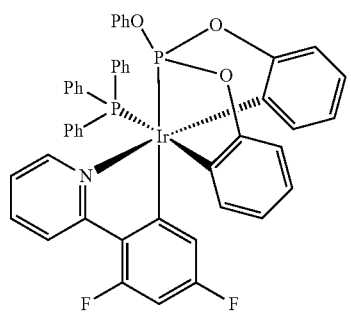

wherein Ph is phenyl.

Preferably, the complex is represented by the following formula:

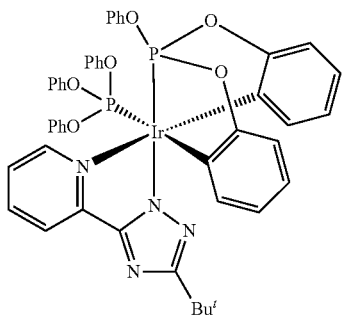

wherein Ph is phenyl, and $Bu^t$ is tert-butyl.

Preferably, the complex is represented by the following formula:

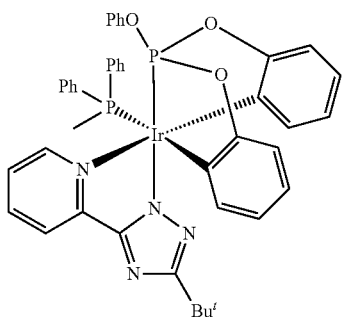

wherein Ph is phenyl, and $Bu^t$ is tert-butyl.

Preferably, the complex is represented by the following formula:

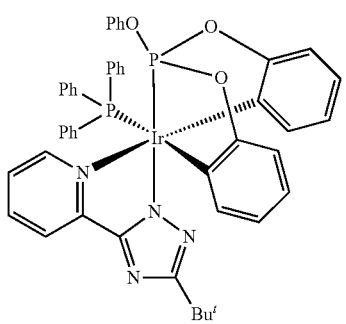

wherein Ph is phenyl, and $Bu^t$ is tert-butyl.

Preferably, the complex is represented by the following formula:

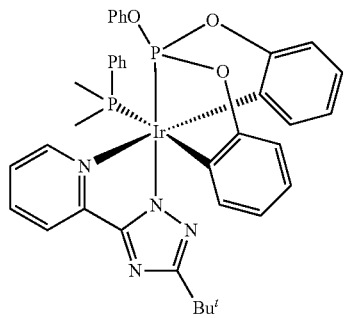

wherein Ph is phenyl, and Bu$^t$ is tert-butyl.

Preferably, the complex is represented by the following formula:

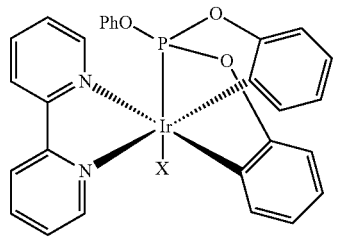

wherein Ph is phenyl, and X=chloride and thiocyanate

Preferably, the complex is represented by the following formula:

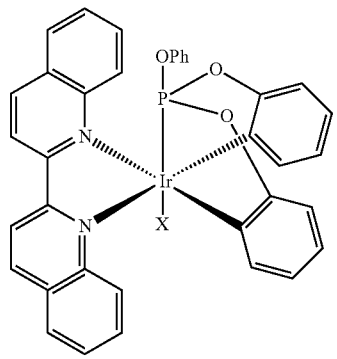

wherein Ph is phenyl and X=chloride and thiocyanate.

Alternatively, the carbon atom (C) and phosphorous atom (P) and carbon atom (C) linked with two arches (C^P^C) in the formulas Ia, Ib and Ic may have a formula of PR$^4$(CH$_2$Ar$^5$)$_2$, i.e. a methylene linker in place of the oxygen linker.

The present invention also discloses an organic light emitting diode, which comprises: a positive electrode formed on a substrate; a negative electrode; and a light emitting layer disposed between said positive electrode and said negative electrode, wherein said light emitting layer comprises the complex of the present invention as an electrophosphorescent material.

DETAILED DESCRIPTION OF THE INVENTION

Figure 1:
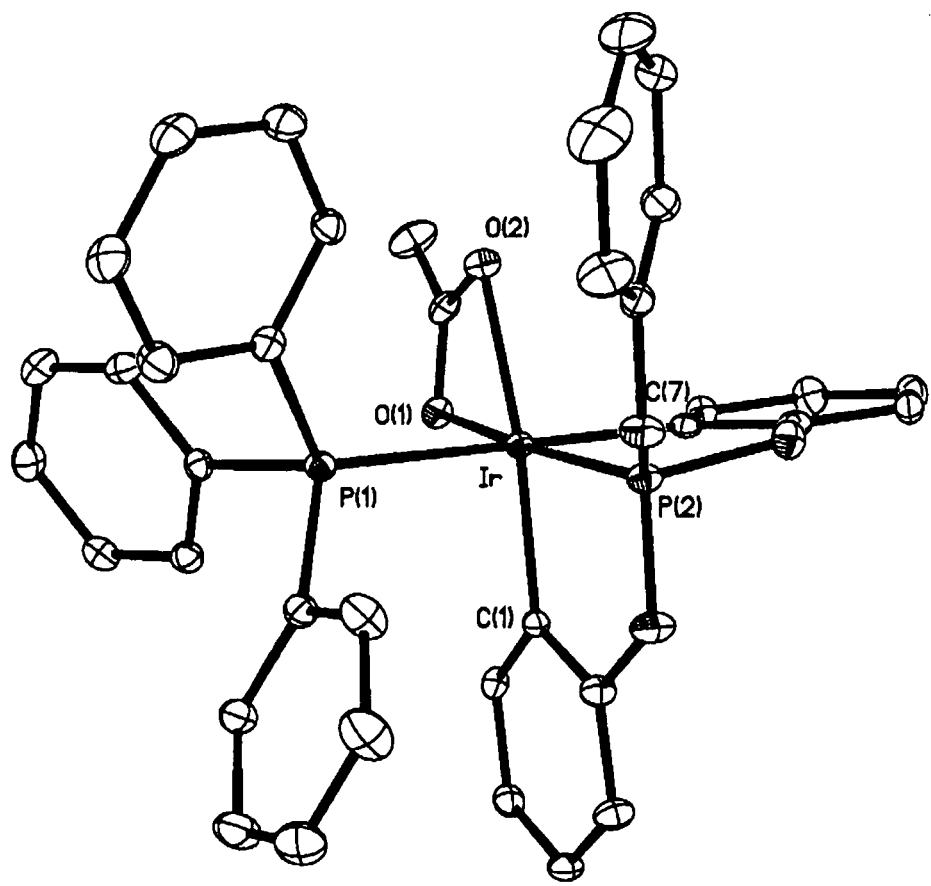
FIG. 1 shows the X-ray structure of Ir complex (1) synthesized in Example 1 according to the present invention, which is an ORTEP diagram of (1) with thermal ellipsoids shown at 30% probability level; bond lengths: Ir—C(1)=2.016(3), Ir—C(7)=2.074(3), Ir—O(1)=2.137(2), Ir—P(2)=2.1421(8), Ir—O(2)=2.236(2) and Ir—P(1)=2.3775(8) Å.

The present invention provides transition metal complexes with a carbon-phosphorus-carbon (C^P^C) tridentate chelate, i.e. di-cyclometalated phosphinite chelate having the aforementioned structures Ia, Ib, Ic, or their stereo isomers. The chelating ligands that coordinated to the central metal atom include one carbon-phosphorus-carbon (C^P^C) tridentate chelate, one carbon-nitrogen (C^N) or azolate-nitrogen (A^N) monoanionic bidentate chromophoric ligand, and one arbitrary charge-neutral donor group (L), while the second arrangement comprises one carbon-phosphorus-carbon (C^P^C) tridentate chelate, one neutral diimine type (N^N) chromophoric chelate, and one arbitrary anionic donor ligand (X). Definition of chromophoric chelates follows that of the traditional concepts, namely: part of a metal-chelate fragment which is responsible for its visible color and/or respective emission. Moreover, when a metal complex with at least one chromophoric chelate absorbs certain kind of energy from light source or electrical power supply, thus energy can be converted by exciting an electron from its ground state into an excited state, for which the frontier orbitals are principally localized in the region of chromophoric chelate(s) of the phosphorescent metal complexes. Typical chromophoric chelates, such as (C^N), (A^N) and (N^N) chelates mentioned in the present invention, comprise aromatic, polyaromatic, or heterocyclic molecules that possess extensive π-conjugation over the whole chelating ligand.

The chromophoric chelate utilized in the present study can be classified into two kinds. The first class is denoted as (C^N)H, which comprise a nitrogen donor segment such as pyridine, isoquinoline and quinazoline as well as an aromatic (aryl group) or functionalized aromatic moiety that can react with the metal reagent via direct C—H activation, giving the so-called cyclometalated chelates. The second class is subsequently named as (A^N)H chelate, which possesses the neutral N-donor segment plus a second fragment with an azolic N—H functional group, the latter can react with central metal ion in a fashion similar to the C—H activation occurred for the (C^N)H chelate, giving formation of an anionic (A^N) chelate. Examples of this chromophoric ligand upon coordination to the metal center are listed below:

(C^N) chelates

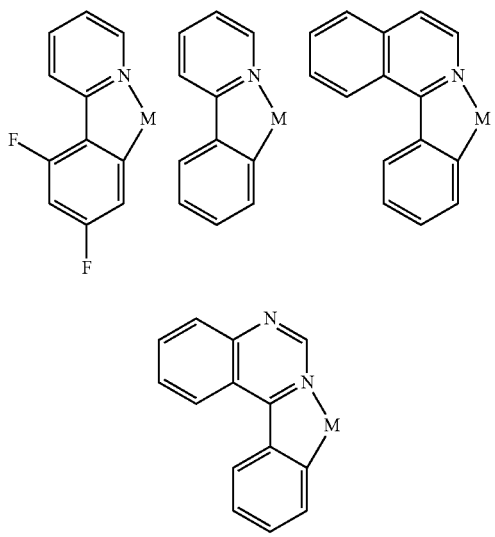

(A^N) chelates

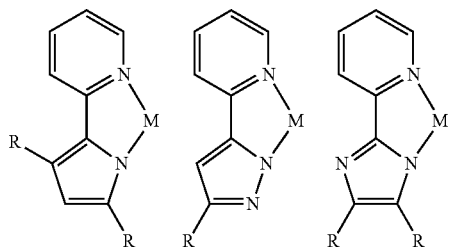

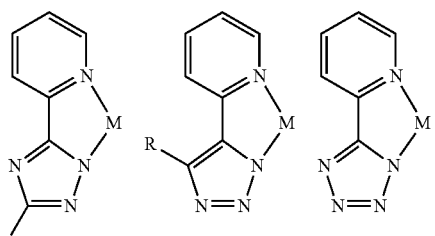

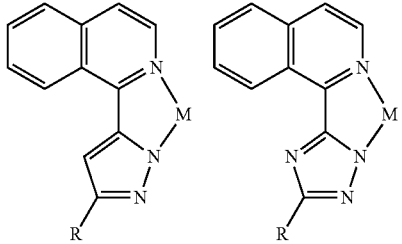

Preferred iridium (III) complexes of the present invention can be synthesized according to processes as shown in Scheme 1:

Scheme 1

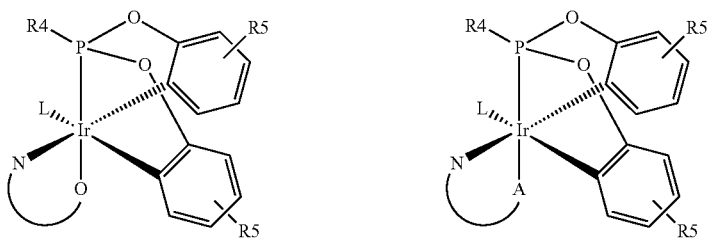

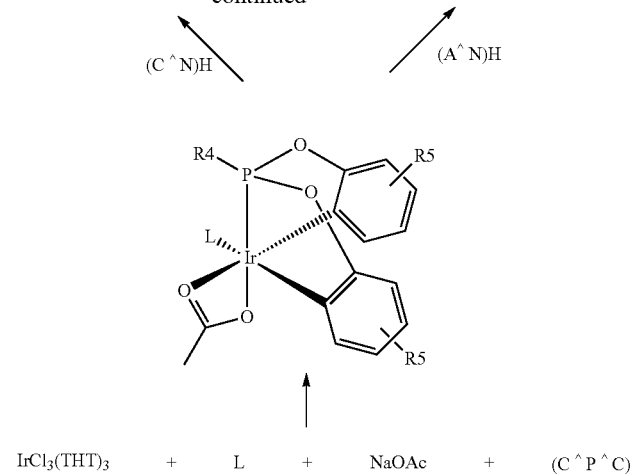

IrCl₃(THT)₃ + L + NaOAc + (C^P^C)

L = phospine with formula PR1R2R3

1. R1 = R2 = R3 = phenoxyl or methoxyl
2. R1 = R2 = R3 = alkyl, aryl
3. R1 = R2 = alkyl, while R3 = aryl group
4. R1 = alkyl, while R2 = R3 = aryl group
5. 4-Ethyl-1-phospha-2,6,7-trioxablcyclo [2.2.2]octane Specific examples 1. R1 = R2 = R3 = OPh
2. R1 = R2 = R3 = OMe
3. R1 = R2 = R3 = Ph
4. R1 = R2 = Ph, R3 = Me
5. R1 = Ph, R2 = R3 = Me (C^P^C) = phosphinite with formula PR4(OAr)₂

Specific examples

1. R4 = Ph, OPh, OMe
2. Ar = phenyl group with R5 substituent
3. R5 = H, alkyl, halide, cyano group In Scheme 1, an iridium reagent IrCl₃(THT)₃, THT=tetrahydrothiophene, was selected due to its increased solubility in high boiling hydrocarbon solvent such as decalin. Thus, treatment of IrCl₃(THT)₃ with one equiv. of (C^P^C) (i.e. tridentate chelating phosphinite with formula PR4(OAr)₂, and another one equiv. of L (i.e. phosphine or phosphinite ligand with formula PR1R2R3) in presence of excess of sodium acetate would give isolation of the intermediate [Ir(L)(C^P^C)(OAc)] in high yield. Subsequent treatment of [Ir(L)(C^P^C)(OAc)] with equal amount of (C^N)H chelate or (A^N)H chelate produced the expected ligand exchange and formation of [Ir(L)(C^P^C) (C^N)] or [Ir(L)(C^P^C)(A^N)] in moderate yields. Alternatively, the reaction can be simplified by skipping isolation of reaction intermediate [Ir(L)(C^P^C) (OAc)]; thus, a one-pot procedure can be attained by further lowering the cost for its production.

Another preferred iridium (III) complexes of the present invention can be synthesized according to processes as shown in Scheme 2:

Scheme 2

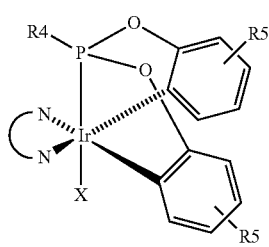

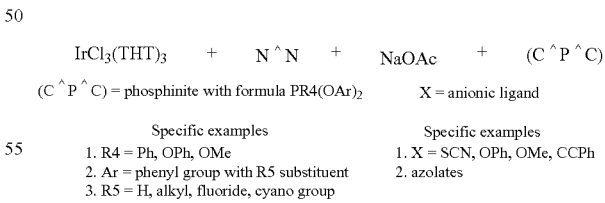

IrCl₃(THT)₃ + N^N + NaOAc + (C^P^C)

(C^P^C) = phosphinite with formula PR4(OAr)₂    X = anionic ligand

Specific examples
1. R4 = Ph, OPh, OMe
2. Ar = phenyl group with R5 substituent
3. R5 = H, alkyl, fluoride, cyano group Specific examples
1. X = SCN, OPh, OMe, CCPh
2. azolates In Scheme 2, the iridium reagent IrCl₃(THT)₃ was again selected due to its increased solubility in high boiling hydrocarbon solvent such as decalin. Thus, treatment of IrCl₃(THT)₃ with one equiv. of (C^P^C) phosphinite of formula PR4(OAr)₂, and one equiv. of charge neutral, diimine N^N chelate in presence of excess of sodium acetate and the mixture was heated at 180° C. for 8 hour. After cooling to RT, the solvent was removed and the residue was purified by silica gel column chromatography. The product can be obtain as [(N^N)

Ir(C^P^C)Cl] in moderate yields. Furthermore, [(N^N)Ir (C^P^C)Cl] and ten equiv. of X⁻ (i.e. inorganic or organic anion) were combined in DMF (15 mL) and the mixture was refluxed for 32 hour. After cooling to RT, the solvent was removed and the residue was purified by silica gel column chromatography. The final product can be obtain as [(N^N)Ir (C^P^C)X] in moderate yields.

In the following text, the synthesis and spectral data of the phosphorescent Ir complexes according to the present invention are described in detail, as well as the application of this type of complexes as a phosphorescent material of an organic light-emitting diode (OLED).

EXAMPLES

General Experimental Procedures. All reactions were performed under a nitrogen atmosphere using anhydrous solvents or solvents treated with an appropriate drying reagent. Mass spectra were obtained on a JEOL SX-102A instrument operating in electron impact (EI) mode or fast atom bombardment (FAB) mode. $^1$H and $^{19}$F NMR spectra were recorded on Varian Mercury-400 or INOVA-500 instruments.

X-Ray Diffraction Studies. Single crystal X-ray diffraction data were measured on a Bruker SMART Apex CCD diffractometer using (Mo—K$_\alpha$) radiation ($\lambda$=0.71073 Å). The data collection was executed using the SMART program. Cell refinement and data reduction were performed with the SAINT program. The structure was determined using the SHELXTL/PC program and refined using full-matrix least squares.

Spectral and dynamic measurement. Steady-state absorption and emission spectra were recorded by a Hitachi (U-3310) spectrophotometer and an Edinburgh (FS920) fluorimeter, respectively. Emission quantum yields were measured at excitation wavelength $\lambda_{ex}$=350 nm in CH$_2$Cl$_2$ at room temperature. In this approach, Quinine sulfate with an emission yield of Φ~0.54±0.2 in 1.0 N sulfuric acid solution served as the standard to calculate the emission quantum yield. Lifetime studies were performed by an Edinburgh FL 900 photon counting system with a hydrogen-filled or a nitrogen lamp as the excitation source. Data were analyzed using a nonlinear least squares procedure in combination with an iterative convolution method. The emission decays were analyzed by the sum of exponential functions, which allows partial removal of the instrument time broadening and consequently renders a temporal resolution of ~200 ps.

Example 1

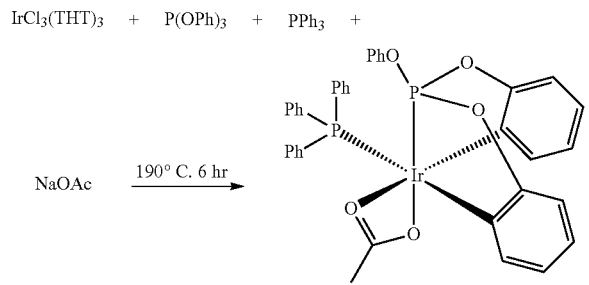

Synthesis of [Ir(tpp)(tpit)(OAc)] (1): IrCl$_3$(THT)$_3$ (110 mg, 0.20 mmol), triphenyl phosphinite (tpit, 62 mg, 0.20 mmol), triphenyl phosphine (tpp, 53 mg, 0.20 mmol), and sodium acetate (82 mg, 1.00 mmol) were combined in decalin (15 mL). The mixture was heated at 190° C. for 6 hour. After cooling to RT and removal of solvent, the residue was purified by silica gel column chromatography using a 1:1 mixture of ethyl acetate and hexane as the eluent. The pale yellow crystals of [Ir(tpp)(tpit)(OAc)] were obtained by slow diffusion of hexane into a saturated CH$_2$Cl$_2$ solution at RT (131 mg, 0.16 mmol, 80%).

Spectral data of [Ir(tpp)(tpit)(OAc)]: MS (FAB, $^{193}$Ir): m/z 763 (M-OAc)⁺; $^1$H NMR (500 MHz, CDCl$_3$, 294K): δ 7.40~7.37 (m, 1H), 7.36~7.33 (m, 3H), 7.30~7.16 (m, 15H), 7.07 (d, J=8.0 Hz, 1H), 6.95~6.89 (m, 5H), 6.58 (td, J=7.5 1.0 Hz, 1H), 5.52 (d, J=8.0 Hz, 1H), 6.43 (td, J=7.0, 1.0 Hz, 1H), 1.45 (s, 3H). $^{31}$P-{$^1$H} NMR (202 MHz, CDCl$_3$, 294K): δ 111.66 (d, J=9.7 Hz, 1P), 12.37 (d, J=9.7 Hz, 1P).

Example 2

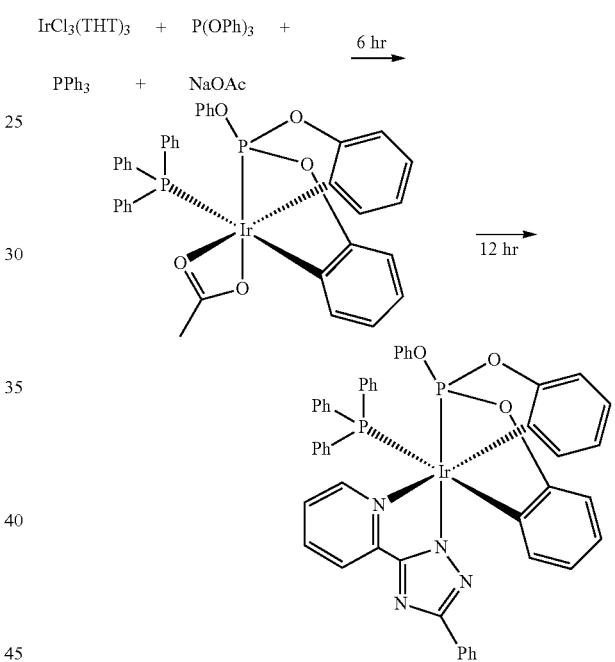

Synthesis of [Ir(tpp)(tpit)(pptz)] (2): IrCl$_3$(THT)$_3$ (110 mg, 0.20 mmol), triphenyl phosphinite (62 mg, 0.20 mmol), triphenyl phosphine (53 mg, 0.20 mmol), and sodium acetate (82 mg, 1.00 mmol) were combined in decalin (15 mL) and the mixture was heated at 190° C. for 6 hours. After cooling to RT, 3-phenyl-5-pyridyl-1,2,4-triazole (pptzH) (48 mg, 0.22 mmol) was added and mixture was heated at 190° C. for 12 hours. Finally, the solvent was removed and the residue was purified by silica gel column chromatography using a 3:1 mixture of ethyl acetate and hexane as the eluent. The colorless crystals of [Ir(tpp)(tpit)(pptz)] were obtained by slow diffusion of hexane into a CH$_2$Cl$_2$ solution at RT (97 mg, 0.10 mmol, 48%).

Spectral data of [Ir(tpp)(tpit)(pptz)]: MS (FAB, $^{193}$IR): m/z 985 (M+1)⁺; $^1$H NMR (500 MHz, CDCl$_3$, 294K): δ 9.02 (d, J=6.0 Hz, 1H), 8.41 (d, J=6.5 Hz, 1H), 7.86 (br, 1H), 7.54~7.49 (m, 3H), 7.43~7.37 (m, 3H), 7.28 (t, J=7.5 Hz, 1H), 7.19~7.17 (m, 3H), 7.10~7.01 (m, 16H), 6.87~6.83 (m, 2H), 6.76~6.71 (m, 3H), 6.62 (t, J=7.5 Hz, 1H), 6.34 (t, J=7.5 Hz, 2H), 6.01 (t, J=6.0 Hz, 2H). $^{31}$P-{$^1$H} NMR (202 MHz, CDCl$_3$, 294K): δ 123.38 (br, 1P), −11.15 (d, J=12.9 Hz, 1P).

Example 3

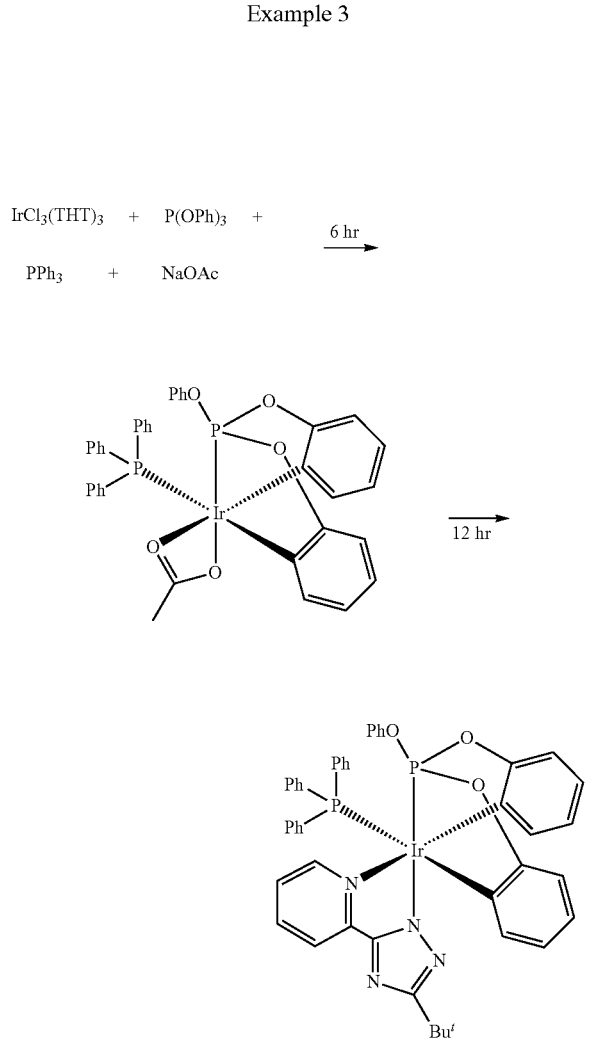

Synthesis of [Ir(tpp)(tpit)(bptz)] (3): IrCl$_3$(THT)$_3$ (110 mg, 0.20 mmol), triphenyl phosphinite (62 mg, 0.20 mmol), triphenyl phosphine (53 mg, 0.20 mmol), and sodium acetate (164 mg, 2.00 mmol) were combined in decalin (15 mL) and the mixture was heated at 190° C. for 6 hour. After cooling to RT, 3-tert-butyl-5-(2-pyridyl)-1,2,4-triazole (bptzH) (45 mg, 0.22 mmol) was added and mixture was heated at 190° C. for 12 hours. Finally, the solvent was removed and the residue was purified by silica gel column chromatography using a 3:1 mixture of ethyl acetate and hexane as the eluent. The colorless crystals of [Ir(tpp)(tpit)(bptz)] were obtained by slow diffusion of hexane into a CH$_2$Cl$_2$ solution at RT (97 mg, 0.10 mmol, 51%).

Spectral data of [Ir(tpp)(tpit)(bptz)]: MS (FAB, $^{193}$Ir): m/z 965 (M+1)$^+$; $^1$H NMR (500 MHz, CDCl$_3$, 294K): δ 9.12 (d, J=7.0 Hz, 1H), 8.25 (d, J=5.5 Hz, 1H), 7.79 (d, J=7.0 Hz, 1H), 7.43~7.37 (m, 3H), 7.27 (t, J=7.5 Hz, 1H), 7.21~7.18 (m, 3H), 7.13~7.08 (m, 13H), 7.03 (d, J=9.0 Hz, 2H), 6.83~6.78 (m, 2H), 6.71~6.66 (m, 2H), 6.61 (t, J=7.0 Hz, 1H), 6.36 (t, J=7.0 Hz, 1H), 5.76 (t, J=6.5 Hz, 1H), 1.62 (s, 9H). $^{31}$P-{$^1$H} NMR (202 MHz, CDCl$_3$, 294K): δ 124.17 (d, J=12.5 Hz, 1P), −11.79 (d, J=12.5 Hz, 1P).

Example 4

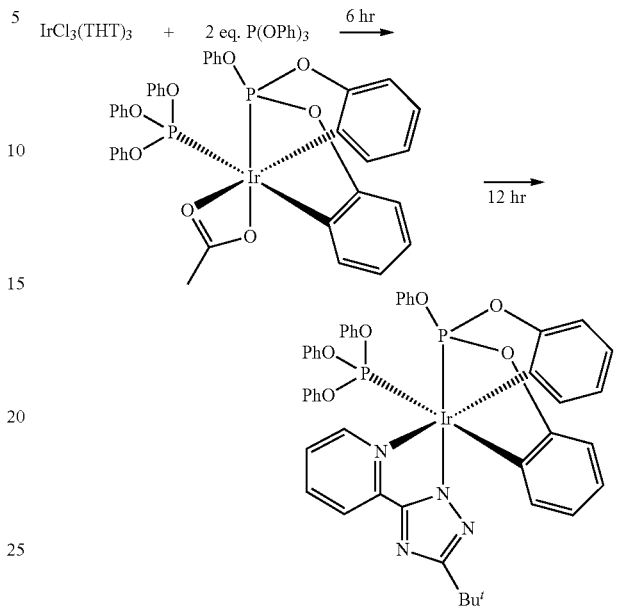

Synthesis of [Ir(tpit)$_2$(bptz)] (4): IrCl$_3$(THT)$_3$ (110 mg, 0.20 mmol), triphenyl phosphinite (tppH, 186 mg, 0.60 mmol), and sodium acetate (164 mg, 2.00 mmol) were combined in degassed decalin (15 mL) and the mixture was heated at 190° C. for 6 hour. After cooling to RT, 3-tert-butyl-5-(2-pyridyl)-1,2,4-triazole (bptzH) (45 mg, 0.22 mmol) was added and mixture was at 190° C. for 12 hour. After cooling to RT and removal of solvent, the residue was purified by silica gel column chromatography using a 1:3 mixture of ethyl acetate and hexane as the eluent. The pale yellow crystals of [Ir(tpit)$_2$(bptz)] were obtained by slow diffusion of hexane into a CH$_2$Cl$_2$ solution at RT (101 mg, 0.10 mmol, 50%).

Spectral data of [Ir(tpit)$_2$(bptz)]: MS (FAB, $^{193}$Ir): m/z 1013 (M+1)$^+$; $^1$H NMR (500 MHz, CDCl$_3$, 294K): δ 9.10 (d, J=5.5 Hz, 1H), 8.24 (d, J=5.5 Hz, 1H), 8.12 (br, 1H), 7.56~7.51 (m, 3H), 7.48 (t, J=8.0 Hz, 2H), 7.33 (t, J=7.5 Hz, 1H), 7.03~6.96 (m, 9H), 6.91~6.86 (m, 2H), 6.82~6.80 (m, 1H), 6.73 (dd, J=8.0, 4.0 Hz, 1H), 7.06 (t, J=7.5 Hz, 1H), 6.57 (t, J=6.0 Hz, 1H), 6.44~6.34 (m, 7H), 5.73 (t, J=8.0 Hz, 1H), 1.59 (s, 9H). $^{31}$P-{$^1$H} NMR (202 MHz, CDCl$_3$, 294K): δ 125.02 (br, 1P), 76.13 (d, J=23.4 Hz, 1P).

Example 5

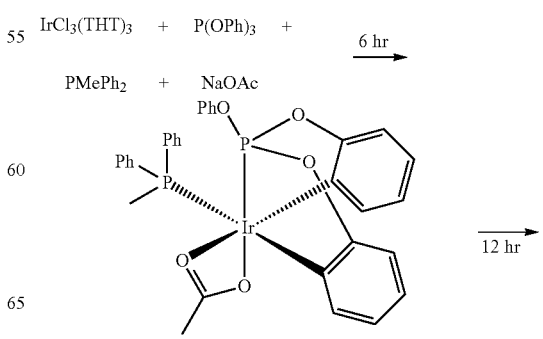

-continued

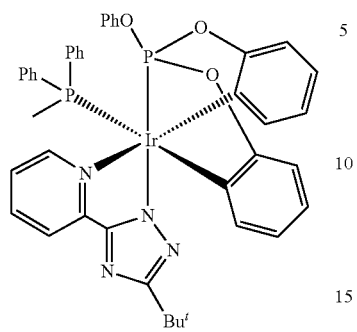

Synthesis of [Ir(mdpp)(tpit)(bptz)] (5): IrCl₃(THT)₃ (110 mg, 0.20 mmol), triphenyl phosphinite (62 mg, 0.20 mmol), methyldiphenylphosphine (mdpp, 40 mg, 0.20 mmol), and sodium acetate (164 mg, 2.00 mmol) were combined in decalin (15 mL) and the mixture was heated at 190° C. for 6 hour. After cooling to RT, 3-tert-butyl-5-(2-pyridyl)-1,2,4-triazole (bptzH) (45 mg, 0.22 mmol) was added and mixture was at 190° C. for 12 hour. After cooling to RT and removal of solvent, the residue was purified by silica gel column chromatography using a 1:3 mixture of ethyl acetate and hexane as the eluent. The pale yellow crystals of [Ir(mdpp)(tpit)(bptz)] were obtained by slow diffusion of hexane into a CH₂Cl₂ solution at RT (98 mg, 0.11 mmol, 54%).

Spectral data of [Ir(mdpp)(tpit)(bptz)]: MS (FAB, ¹⁹³Ir): m/z 903 (M+1)⁺; ¹H NMR (500 MHz, CDCl₃, 294K): δ 9.14 (t, J=7.0 Hz, 1H), 8.23 (d, J=5.5 Hz, 1H), 7.83 (d, J=7.5 Hz, 1H), 7.48~7.43 (m, 3H), 7.34~7.30 (m, 3H), 7.21 (td, J=6.5, 1.0 Hz, 1H), 7.17~7.05 (m, 7H), 6.97 (t, J=9.0 Hz, 2H), 6.89 (t, J=7.5 Hz, 1H), 6.84 (t, J=7.5 Hz, 1H), 6.73 (d, J=8.5 Hz, 2H), 6.65~6.62 (m, 2H), 6.40 (t, J=7.5 Hz, 1H), 5.94 (t, J=6.5 Hz, 1H), 1.62 (s, 9H), 1.61 (d, J=9.0 Hz, 3H). ³¹P-{¹H} NMR (202 MHz, CDCl₃, 294K): δ 126.46 (d, J=11.9 Hz, 1P), −21.67 (d, J=11.9 Hz, 1P).

Example 6

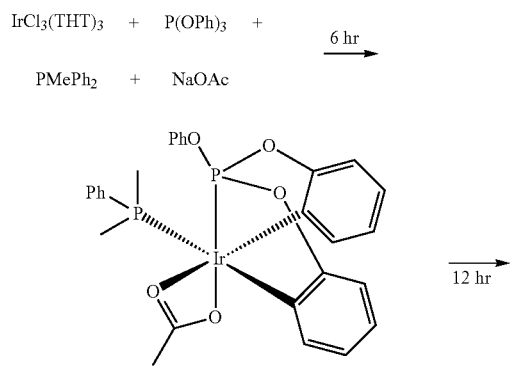

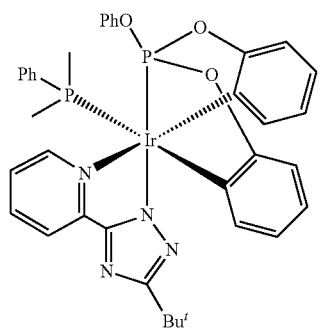

Synthesis of [Ir(dmpp)(tpit)(bptz)] (6): IrCl₃(THT)₃ (110 mg, 0.20 mmol), triphenyl phosphinite (62 mg, 0.20 mmol), dimethylphenylphosphine (dmpp, 28 mg, 0.20 mmol), and sodium acetate (164 mg, 2.00 mmol) were combined in decalin (15 mL) and the mixture was heated at 190° C. for 6 hour. After cooling to RT, 3-tert-butyl-5-(2-pyridyl)-1,2,4-triazole (bptzH) (45 mg, 0.22 mmol) was added and mixture was at 190° C. for 12 hour. After cooling to RT and removal of solvent, the residue was purified by silica gel column chromatography using a 1:3 mixture of ethyl acetate and hexane as the eluent. The pale yellow crystals of [Ir(dmpp)(tpit)(bptz)] were obtained by slow diffusion of hexane into a CH₂Cl₂ solution at RT (76 mg, 0.09 mmol, 45%).

Spectral data of [Ir(dmpp)(tpit)(bptz)]: MS (FAB, ¹⁹³Ir: m/z 841 (M+1)⁺; ¹H NMR (500 MHz, CDCl₃, 294K): δ 9.05 (t, J=6.0 Hz, 1H), 8.23 (d, J=5.5 Hz, 1H), 7.94 (d, J=8.5 Hz, 1H), 7.53~7.46 (m, 5H), 7.36~7.32 (m, 1H), 7.10 (td, J=7.5, 1.0 Hz, 1H), 7.02 (td, J=7.5, 1.0 Hz, 2H), 6.90~6.86 (m, 2H), 6.83~6.81 (m, 1H), 6.73~6.70 (m, 3H), 6.67~6.62 (m, 2H), 6.42 (t, J=7.5 Hz, 1H), 6.07 (td, J=7.0, 1.0 Hz, 1H), 1.62 (s, 9H), 1.40 (d, J=9.0 Hz, 3H), 1.12 (d, J=10.5 Hz, 3H). ³¹P-{¹H} NMR (202 MHz, CDCl₃, 294K): δ 127.79 (d, J=14.1 Hz, 1P), −29.10 (d, J=14.1 Hz, 1P).

Example 7

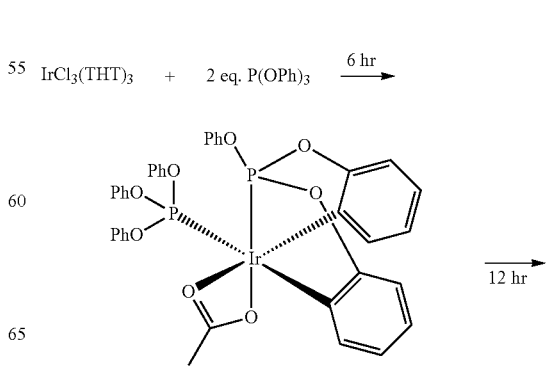

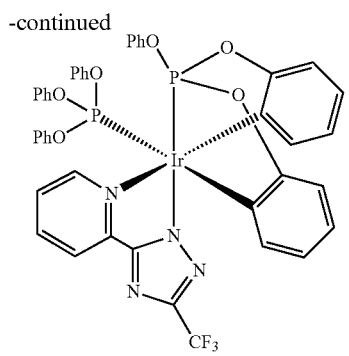

Synthesis of [Ir(tpit)₂(fptz)] (7): IrCl₃(THT)₃ (110 mg, 0.20 mmol), triphenyl phosphinite (tppH, 136 mg, 0.44 mmol), and sodium acetate (164 mg, 2.00 mmol) were combined in degassed decalin (15 mL) and the mixture was heated at 190° C. for 6 hour. After cooling to RT, 3-trifluoromethyl-5-(2-pyridyl)-1,2,4-triazole (fptzH) (47 mg, 0.22 mmol) was added and mixture was at 190° C. for 12 hour. After cooling to RT and removal of solvent, the residue was purified by silica gel column chromatography using a 3:1 mixture of ethyl acetate and hexane as the eluent. The pale yellow crystals of [Ir(tpit)₂(fptz)] were obtained by slow diffusion of hexane into a CH₂Cl₂ solution at RT (92 mg, 0.09 mmol, 45%).

Spectral data of [Ir(tpit)₂(bptz)]: MS (FAB, $^{193}$Ir): m/z 1025 (M+1)⁺; ¹H NMR (500 MHz, CDCl₃, 294K): δ 8.83 (d, J=7.0 Hz, 1H), 8.46 (d, J=5.5 Hz, 1H), 8.04 (d, J=8.0 Hz, 1H), 7.64 (t, J=7.0 Hz, 1H), 7.55 (d, J=9.0 Hz, 2H), 7.49 (t, J=8.0 Hz, 2H), 7.35 (t, J=7.0 Hz, 1H), 7.04~6.97 (m, 9H), 6.94~6.89 (m, 2H), 6.82~6.80 (m, 2H), 6.75 (dd, J=7.5, 4.0 Hz, 1H), 6.69 (t, J=7.0 Hz, 1H), 6.46 (t, J=8.0 Hz, 6H), 6.42 (t, J=8.0 Hz, 1H), 5.72 (t, J=8.0 Hz, 1H). ¹⁹F-{¹H} NMR (470 MHz, CDCl₃, 294K): δ −63.71(s, 3F). ³¹P-{¹H} NMR (202 MHz, CDCl₃, 294K): δ 122.66 (d, J=25.8 Hz, 1P), 75.45 (d, J=25.8 Hz, 1P).

Example 8

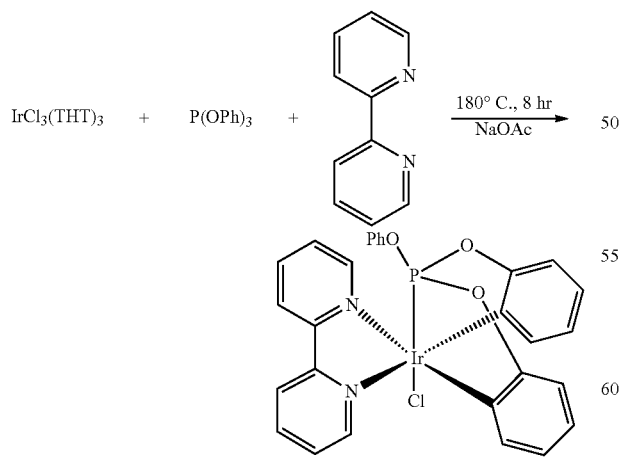

Synthesis of [Ir(bpy)(tpit)Cl] (8): IrCl₃(THT)₃ (110 mg, 0.20 mmol), triphenyl phosphinite (tpit, 62 mg, 0.20 mmol), 2,2'-bipyridine (bpy, 31 mg, 0.20 mmol), and sodium acetate (82 mg, 1.00 mmol) were combined in decalin (15 mL) and the mixture was heated at 180° C. for 8 hour. After cooling to RT, the solvent was removed and the residue was purified by silica gel column chromatography using a 3:1 mixture of CH₂Cl₂ and ethyl acetate as the eluent. The green crystals of [Ir(bpy)(tpit)Cl] were obtained by slow diffusion of hexane into a CH₂Cl₂ solution at RT (88 mg, 0.13 mmol, 64%).

Spectral data of [Ir(bpy)(tpit)Cl]: MS (FAB, $^{193}$Ir): m/z 657 (M-Cl)⁺; ¹H NMR (500 MHz, CDCl₃, 294K): δ 8.18 (d, J=7.0 Hz, 2H), 8.00 (d, J=5.0 Hz, 2H), 7.86~7.80 (m, 4H), 7.24 (t, J=6.0 Hz, 2H), 6.98~6.96 (m, 4H), 6.90~6.87 (m, 2H), 6.78 (t, J=7.5 Hz, 1H), 6.61 (t, J=8.0 Hz, 1H), 6.51 (d, J=8.0 Hz, 1H). ³¹P-{¹H} NMR (202 MHz, CDCl₃, 294K): δ 118.95 (s, 1P).

Example 9

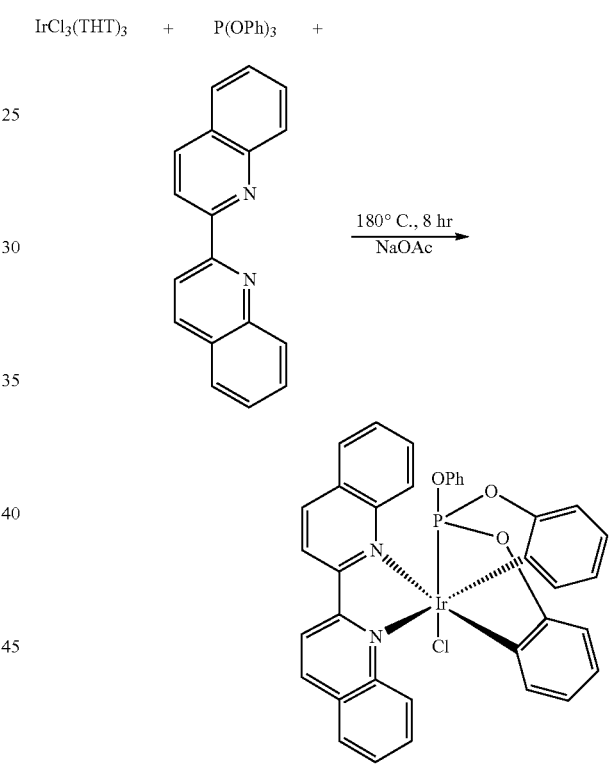

Synthesis of [Ir(bq)(tpit)Cl] (9): IrCl₃(THT)₃ (110 mg, 0.20 mmol), triphenyl phosphinite (tpit, 62 mg, 0.20 mmol), 2,2'-biquinoline (bpy, 52 mg, 0.20 mmol), and sodium acetate (82 mg, 1.00 mmol) were combined in decalin (15 mL) and the mixture was heated at 180° C. for 8 hour. After cooling to RT, the solvent was removed and the residue was purified by silica gel column chromatography using a 3:1 mixture of CH₂Cl₂ and ethyl acetate as the eluent. The green crystals of [Ir(bq)(tpit)Cl] were obtained by slow diffusion of hexane into a CH₂Cl₂ solution at RT (56 mg, 0.08 mmol, 42%).

Spectral data of [Ir(bq)(tpit)C1]: MS (FAB, $^{193}$I0: m/z 664 (M-Cl)⁺; ¹H NMR (500 MHz, CDCl₃, 294K): δ 8.49 (d, J=9.5 Hz, 2H), 8.25 (d, J=5.0 Hz, 1H), 8.23 (d, J=9.5 Hz, 3H), 7.97 (d, J=8.5 Hz, 2H), 7.70 (d, J=8.0 Hz, 2H), 7.46 (t, J=7.5 Hz, 2H), 7.27 (t, J=8.0 Hz, 2H), 6.84~6.83 (m, 4H), 6.76~6.74 (m, 2H), 6.71 (t, J=7.5 Hz, 1H), 6.32 (t, J=8.0 Hz, 2H), 6.51 (d, J=8.0 Hz, 2H). $^{31}P-\{^1H\}$ NMR (202 MHz, CDCl$_3$, 294K): δ 113.43 (s, 1P).

Example 10

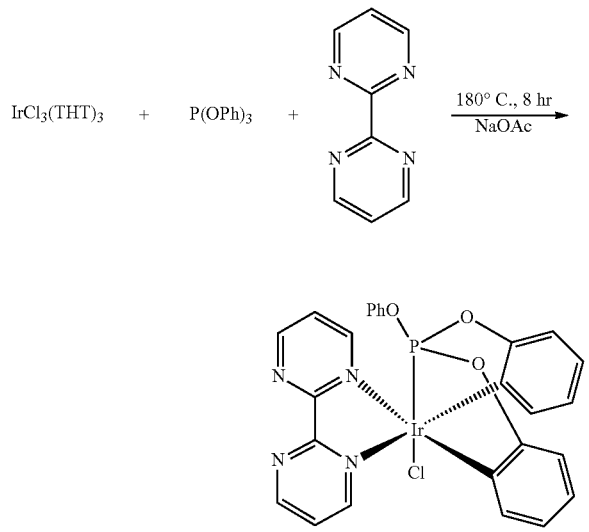

Synthesis of [Ir(bpym)(tpit)] (10): IrCl$_3$(THT)$_3$ (110 mg, 0.20 mmol), triphenyl phosphinite (tpit, 62 mg, 0.20 mmol), 2,2'-bipyrimidine (bpym, 32 mg, 0.20 mmol), and sodium acetate (82 mg, 1.00 mmol) were combined in decalin (15 mL) and the mixture was heated at 180° C. for 8 hour. After cooling to RT, the solvent was removed and the residue was purified by silica gel column chromatography using a 3:1 mixture of CH$_2$Cl$_2$ and ethyl acetate as the eluent. The yellow crystals of [Ir(bpym)(tpit)Cl] were obtained by slow diffusion of hexane into a CH$_2$Cl$_2$ solution at RT (19 mg, 0.03 mmol, 16%).

Spectral data of [Ir(bpym)(tpit)Cl]: MS (FAB, $^{193}$Ir: m/z 566 (M-Cl)$^+$; $^1$H NMR (500 MHz, CDCl$_3$, 294K): δ 9.00 (dd, J=4.5, 2.0 Hz, 2H), 8.15~8.13 (m, 4H), 7.35 (t, J=5.5 Hz, 2H), 7.02~6.98 (m, 4H), 6.91~6.88 (m, 2H), 6.85~6.81 (m, 3H), 6.52 (d, J=8.0 Hz, 2H). $^{31}P-\{^1H\}$ NMR (202 MHz, CDCl$_3$, 294K): δ 119.16 (s, 1P).

Example 11

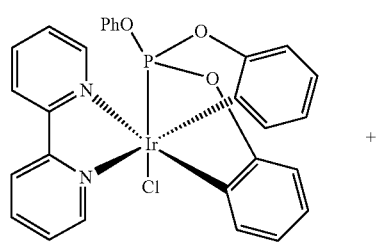

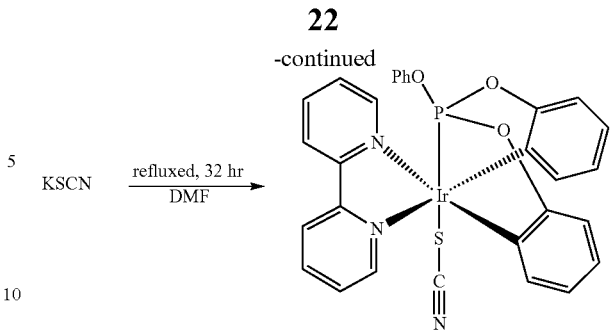

Synthesis of [Ir(bpy)(tpit)SCN] (11): Ir(bpy)(tpit)Cl (50 mg, 0.07 mmol) and KSCN(70 mg, 0.7 mmol) were combined in DMF (15 mL) and the mixture was refluxed for 32 hour. After cooling to RT, the solvent was removed and the residue was purified by silica gel column chromatography using a 1:3 mixture of CH$_2$Cl$_2$ and ethyl acetate as the eluent. The yellowish crystals of [Ir(bpy)(tpit)SCN] were obtained by slow diffusion of hexane into a CH$_2$Cl$_2$ solution at RT (22 mg, 0.03 mmol, 42%).

Spectral data of [Ir(bpy)(tpit)SCN]: MS (FAB, $^{193}$Ir): m/z 715 M$^+$; $^1$H NMR (500 MHz, CDCl$_3$, 294K): δ 7.94 (d, J=5.5 Hz, 2H), 7.90~7.85 (m, 4H), 7.78 (d, J=8.0 Hz, 2H), 7.29(td, J=5.5, 2.5 Hz, 2H), 7.00~6.97 (m, 4H), 6.92 (td, J=7.0, 2.0 Hz, 2H), 6.78 (t, J=7.5 Hz, 1H), 6.72 (t, J=7.5 Hz, 2H), 6.46 (d, J=8.0 Hz, 2H). $^{31}P-\{^1H\}$ NMR (202 MHz, CDCl$_3$, 294K): δ 121.58 (s, 1P).

Example 12

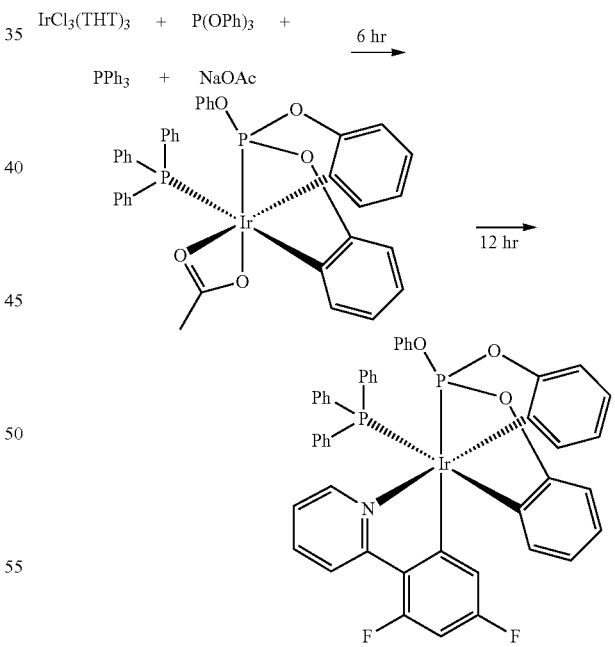

Synthesis of [Ir(tpp)(tpit)(dfppy)] (12): IrCl$_3$(THT)$_3$ (110 mg, 0.20 mmol), triphenyl phosphinite (62 mg, 0.20 mmol), triphenyl phosphine (53 mg, 0.20 mmol), and sodium acetate (164 mg, 2.00 mmol) were combined in decalin (15 mL) and the mixture was heated at 190° C. for 6 hour. After cooling to RT, 4,6-difluorophenyl pyridine (dfppy) (42 mg, 0.22 mmol) was added and mixture was heated at 190° C. for 12 hours. Finally, the solvent was removed and the residue was purified by silica gel column chromatography using a 3:1 mixture of ethyl acetate and hexane as the eluent. The colorless crystals of [Ir(tpp)(tpit)(bptz)] were obtained by slow diffusion of hexane into a $CH_2Cl_2$ solution at RT (23 mg, 0.02 mmol, 12%).

Spectral data of [Ir(tpp)(tpit)(dfppy)]: MS (FAB, $^{193}$Ir): m/z 954 (M+1)$^+$; $^1$H NMR (500 MHz, CDCl$_3$, 294K): δ 9.43 (d, J=5.5 Hz, 1H), 7.70 (d, J=10.5 Hz, 1H), 7.39~7.33 (m, 3H), 7.30~7.26 (m, 5H), 7.21 (d, J=7.5 Hz, 1H), 7.13~7.09 (m, 6H), 7.06~6.98 (m, 9H), 6.92 (d, J=7.5 Hz, 1H), 6.84~6.78 (m, 2H), 6.48 (t, J=7.5 Hz, 1H), 6.44~6.39 (m, 3H), 6.20 (td, J=7.5, 1.5 Hz, 1H). $^{19}$F-{$^1$H} NMR (376 MHz, CDCl$_3$, 294K): δ −110.39(dd, J=14.7, 9.4 Hz, 1F), −110.73(t, J=9.4 Hz, 1F). $^{31}$P-{$^1$H} NMR (202 MHz, CDCl$_3$, 294K): δ 124.91~124.57 (m, 1P), 11.72 (dd, J=19.0, 10.9 Hz, 1P).

Figure 2:
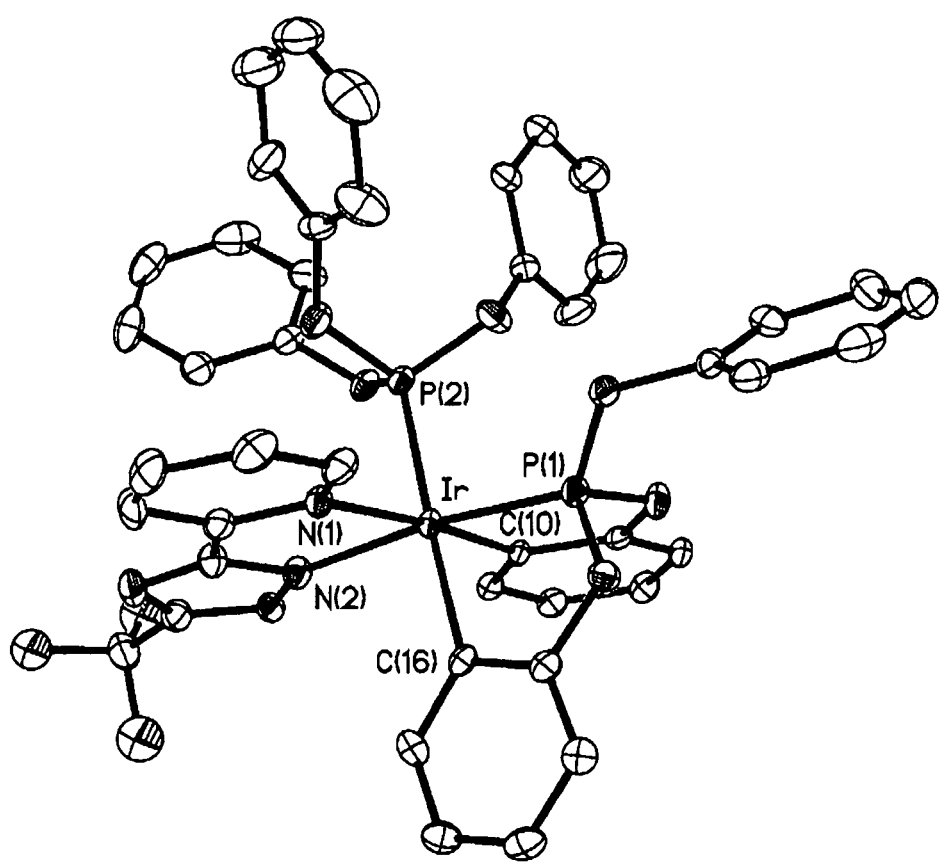
FIG. 2 shows the X-ray structure of Ir complex (7) synthesized in Example 7 according to the present invention, which is an ORTEP diagram of (7) with thermal ellipsoids shown at 30% probability level; bond lengths: Ir—C(10)=2.062(5), Ir—N(2)=2.093(5), Ir—C(16)=2.094(5), Ir—N(1)=2.145(5), Ir—P(1)=2.1708(14) and Ir—P(2)=2.2695(15) Å.
Figure 3:
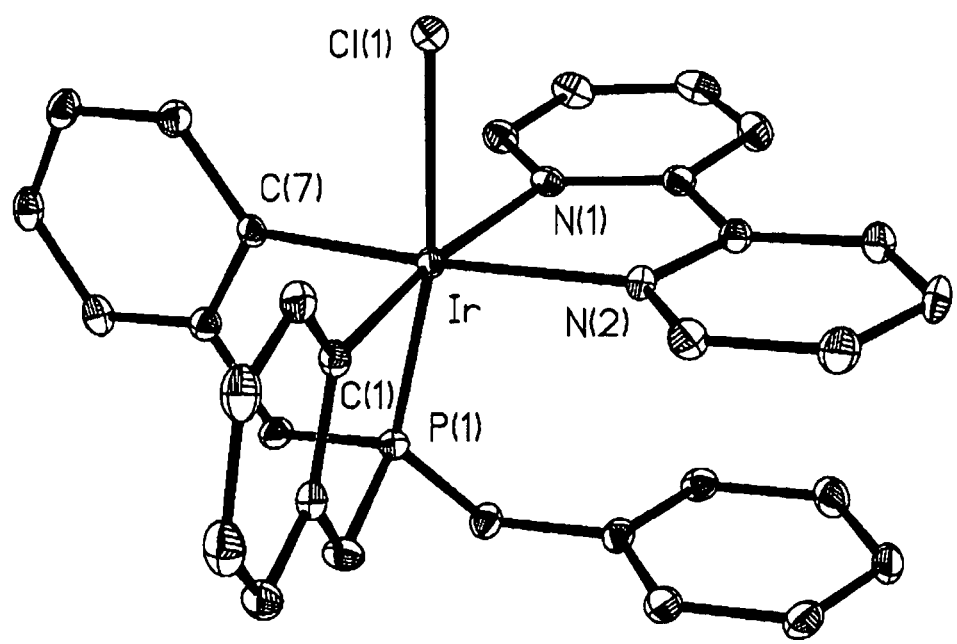
FIG. 3 shows the X-ray structure of Ir complex (8) synthesized in Example 8 according to the present invention, which is an ORTEP diagram of (8) with thermal ellipsoids shown at 30% probability level; bond lengths: Ir—C(7)=2.051(4), Ir—C(1)=2.054(4), Ir—N(1)=2.134(3), Ir—P(1)=2.1441(10), Ir—N(2)=2.145(3) and Ir—Cl(1)=2.4455(9) Å.
Figure 4:
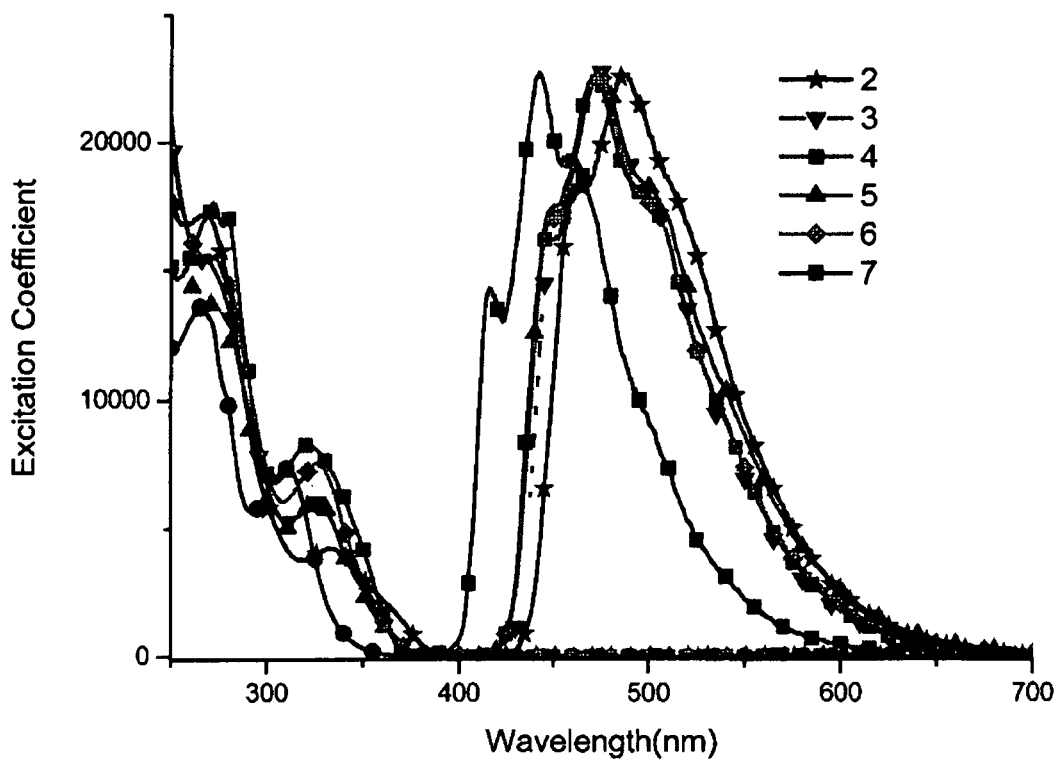
FIG. 4 shows the structural drawings and UV/vis absorption and emission spectra of the complexes (2)-(7) in CH$_2$Cl$_2$ solution, which were prepared in Examples 2-7 according to the present invention.
Figure 4:
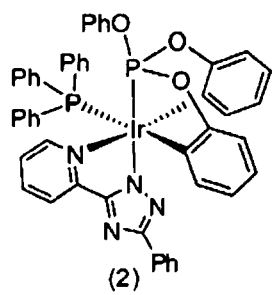
Figure 4:
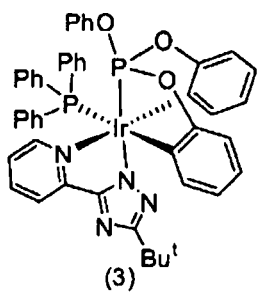
Figure 4:
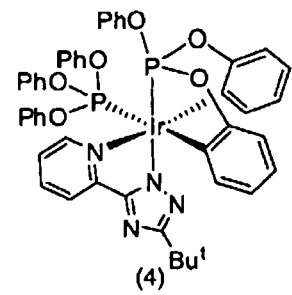
Figure 4:
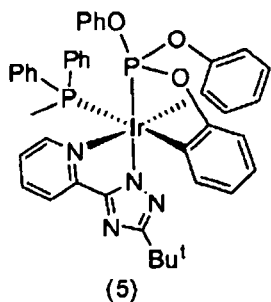
Figure 4:
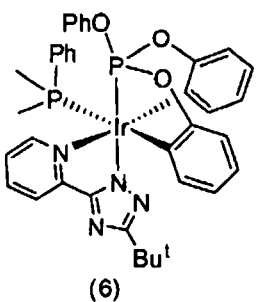
Figure 4:
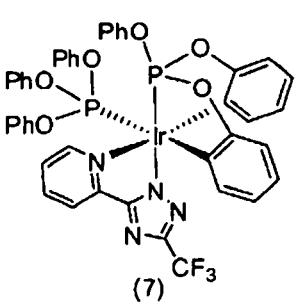
Figure 5:
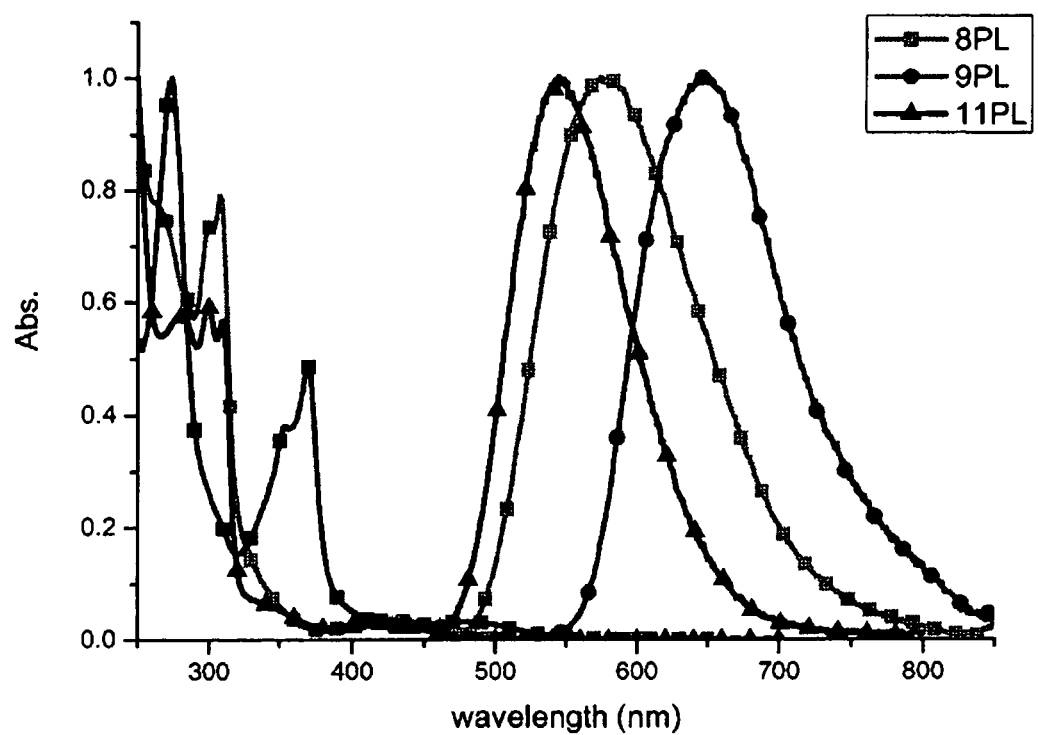
FIG. 5 shows the structural drawings and UV/vis absorption and emission spectra of the complexes (8), (9) and (11) in CH$_2$Cl$_2$ solution, which were prepared in Examples 8-9 according to the present invention.
Figure 5:
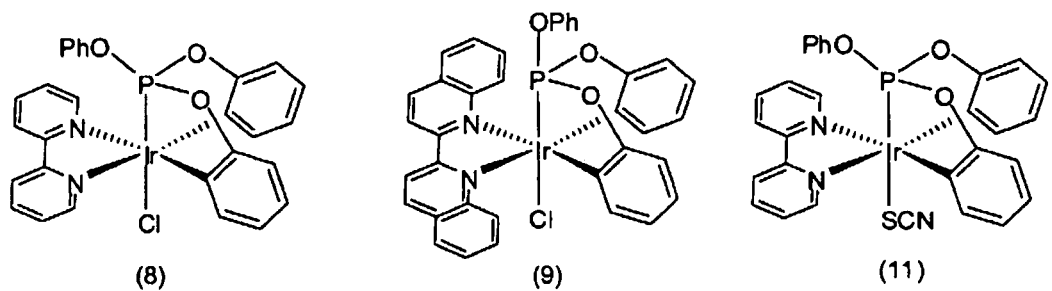

Single crystal X-ray diffraction structure of complexes 1, 7, and 8 are showed in FIGS. 1, 2, and 3, respectively. The photophysical properties of compounds (2) to (9) are listed in Table 1. The absorption and normalized emission spectra of complexes 2-7 and 8-9 recorded in degassed $CH_2Cl_2$ solution at RT are showed in FIGS. 4 and 5.

TABLE 1

| Complex | Emission $\lambda_{max}$ (nm) | Q.E. | $\tau_{obs}$ | $k_r$ (1/s) | $k_{nr}$ (1/s) |
|---|---|---|---|---|---|
| 2 | 462, 486, 509 | 0.22 | 5.5 μs | $4.00 \times 10^4$ | $1.40 \times 10^5$ |
| 3 | 450, 475, 492 | 0.07 | 2.5 μs | $2.80 \times 10^4$ | $3.72 \times 10^5$ |
| 4 | 447, 472, 492 | 0.87 | 44.5 μs | $1.95 \times 10^4$ | $3.00 \times 10^3$ |
| 5 | 450, 473, 498 | 0.34 | 11.1 μs | $3.06 \times 10^4$ | $5.95 \times 10^4$ |
| 6 | 451, 473, 498 | 0.45 | 14.3 μs | $3.15 \times 10^4$ | $3.85 \times 10^4$ |
| 7 | 416, 442, 458 | 0.012 | 243 ns | $4.89 \times 10^4$ | $4.09 \times 10^6$ |
| 8 | 574 | 0.48 | 839 ns | $5.77 \times 10^5$ | $6.15 \times 10^5$ |
| 9 | 646 | 0.11 | 325 ns | $3.39 \times 10^5$ | $2.74 \times 10^6$ |

Example 13

General Method of Producing OLEDs

Synthesized compounds according to this disclosed specification were subject to purification by temperature-gradient sublimation in high vacuum before use in subsequent device studies. OLEDs were fabricated on the ITO-coated glass substrates with multiple organic layers sandwiched between the transparent bottom indium-tin-oxide (ITO) anode and the top metal cathode. The material layers were deposited by vacuum evaporation in a vacuum chamber with a base pressure of <10$^{-6}$ torr. The deposition system permits the fabrication of the complete device structure in a single vacuum pump-down without breaking vacuum. The deposition rate of organic layers was kept at ~0.2 nm/s. The active area of the device is 2×2 mm$^2$, as defined by the shadow mask for cathode deposition.

A blue OLED device structure and materials used were ITO/α-NPD (30 nm)/TCTA (20 nm)/CzSi (3 nm)/CzSi: (4) 8.0 wt. % (35 nm)/UGH2: (4) 8.0 wt. % (3 nm)/UGH2 (2 nm)/BCP (50 nm)/Cs$_2$CO$_3$ (2 nm)/Al, for which α-NPD, TCTA, CzSi, UGH2, and BCP stand for α-naphthylphenyl-biphenyl diamine, 4,4',4"-tri(N-carbazolyl)triphenylamine, 9-(4-tert-butylphenyl)-3,6-bis(triphenylsilyl)-9H-carbazole, p-bis(triphenylsilyl)benzene, and 2,9-dimethyl-4,7-diphenyl-1,10-phenanthroline, respectively. The α-naphthylphenylbiphenyl diamine (α-NPD) and 4,4',4"-tri(N-carbazolyl) triphenylamine (TCTA) were used as the hole-transport layer (HTL). The thin CzSi (30 Å) was served both as the hole-transport layer and as the buffer layer for blocking the high-energy triplet excitons on (4) from migrating to TCTA (with a lower triplet energy). Double emitting layers (CzSi and UGH2 doped with 7.0 wt. % of (4)) were used to achieve better balance between hole and electron injection/transport and thus to move the exciton formation zone away from the quenching interfaces with carrier-transport layers, taking advantage of the hole-transport nature of CzSi and the electron-transport nature of UGH2. The thin UGH2 (20 Å) was served both as the electron-transport/hole-blocking layer and as the buffer layer for blocking the high-energy triplet excitons from migrating to BCP (with a lower triplet energy). Finally, BCP was used as the electron-transport layer, and Al or Cs$_2$CO$_3$ were used as the electron-injection layer.

Figure 6:
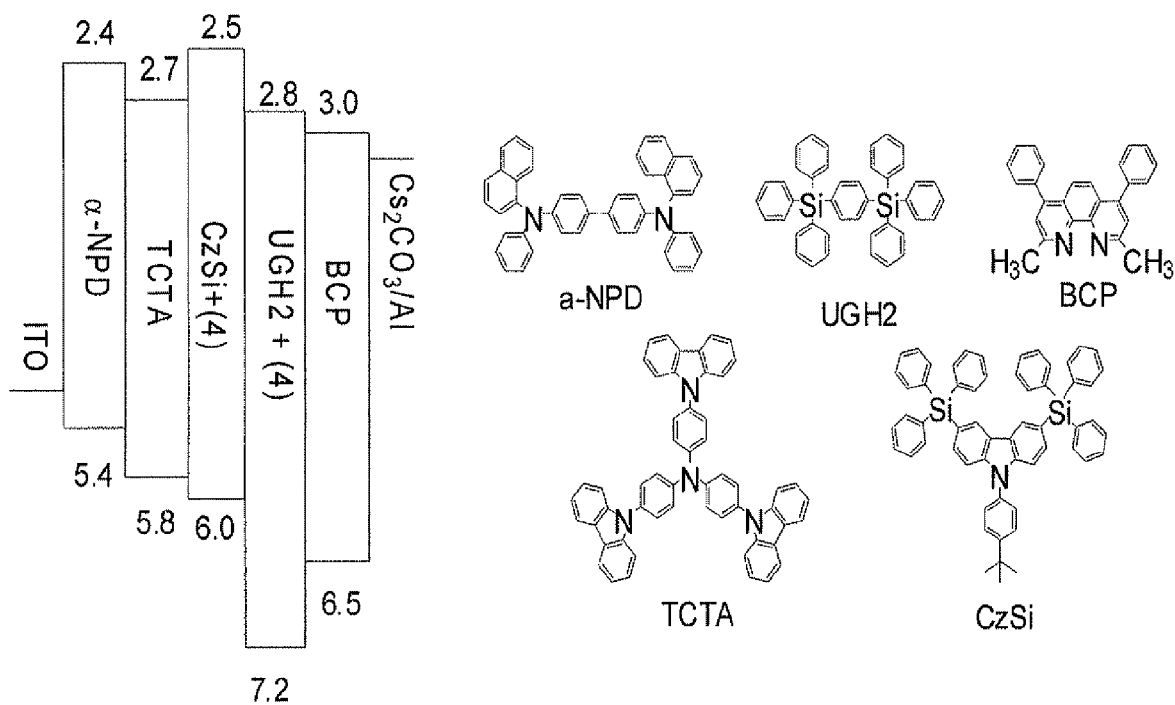
FIG. 6 shows the structure of the blue-emitting OLED fabricated employing Ir complex (4) of the present invention and the structures of the compounds used together with an energy level diagram.
Figure 7A:
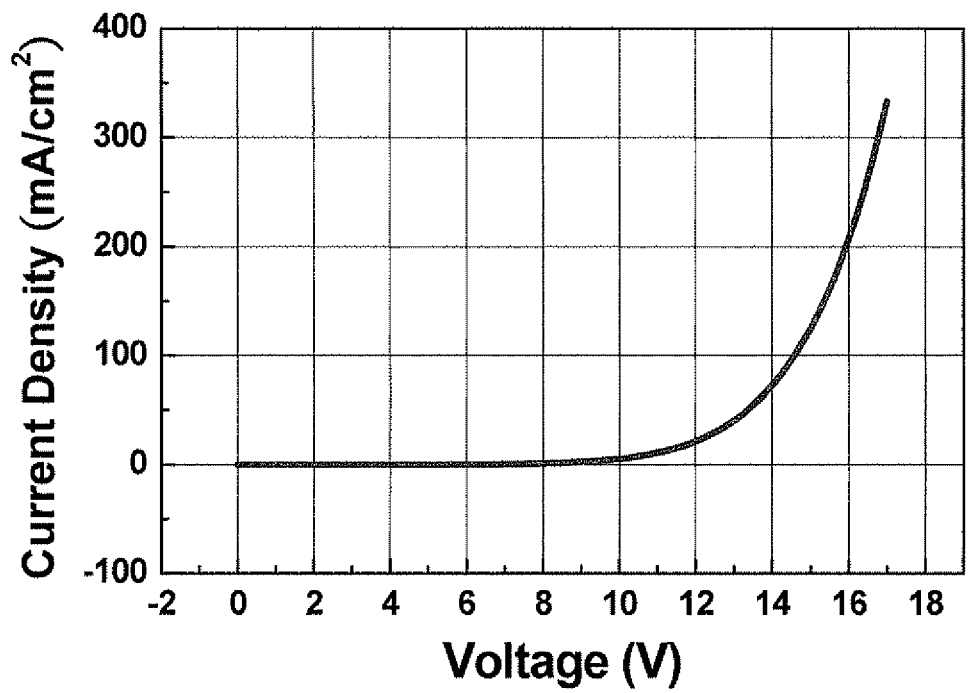
FIG. 7 shows the performance data of the blue OLED fabricated employing Ir complex (4) of the present invention, wherein (a) plot of current density versus driving voltage, (b) plot of external quantum efficiency versus brightness, (c) plot of power efficiency versus brightness, and (b) plot of luminescent efficiency versus brightness.
Figure 7B:
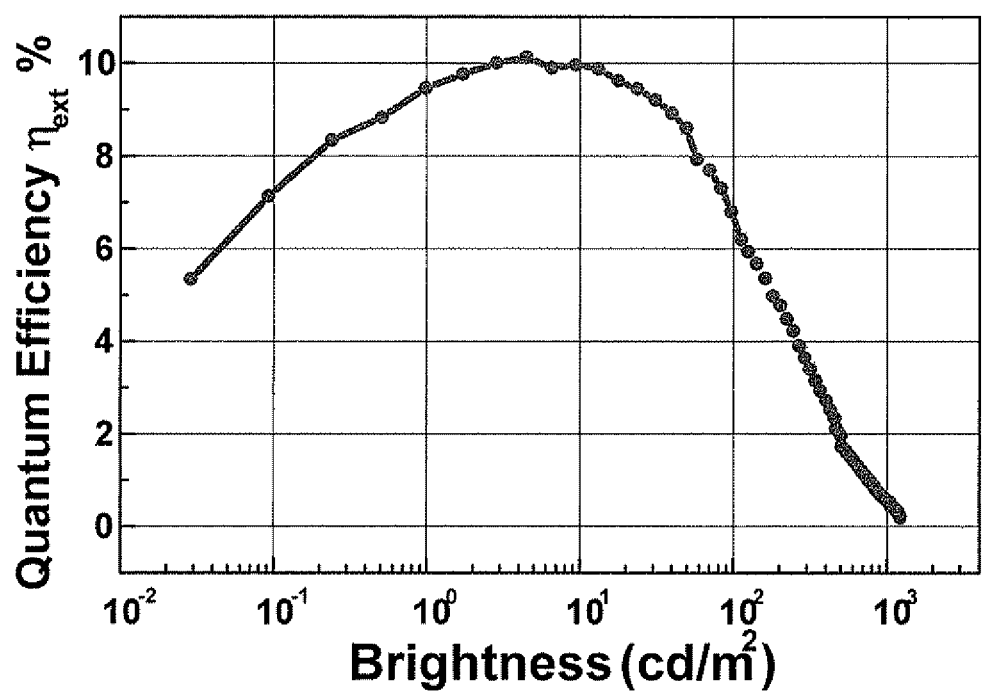
Figure 7C:
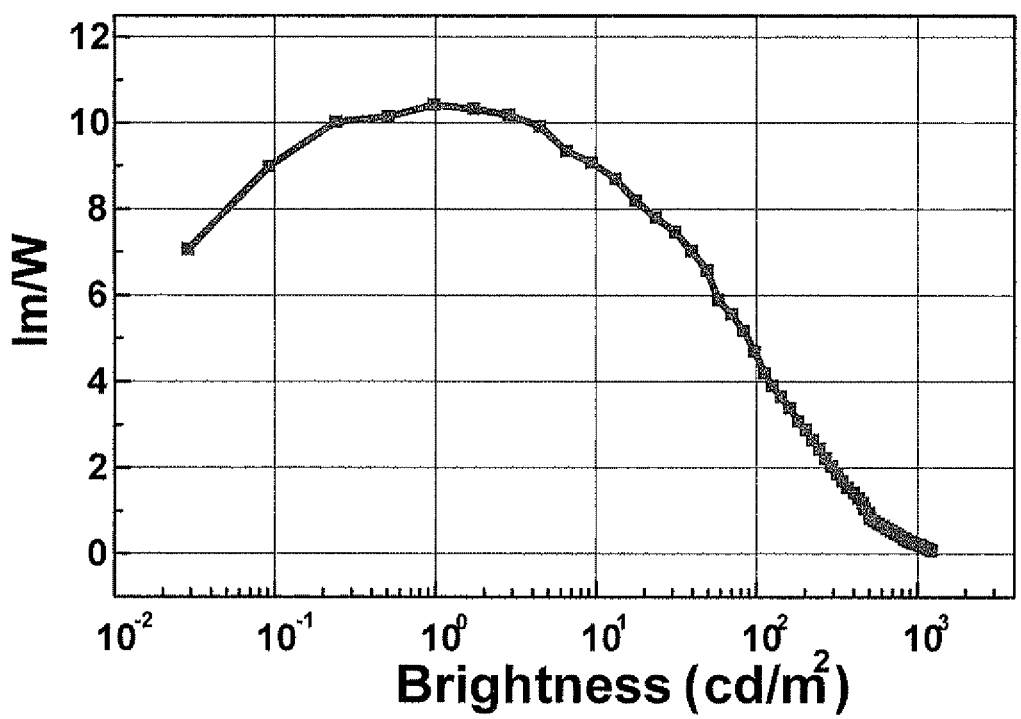
Figure 7D:
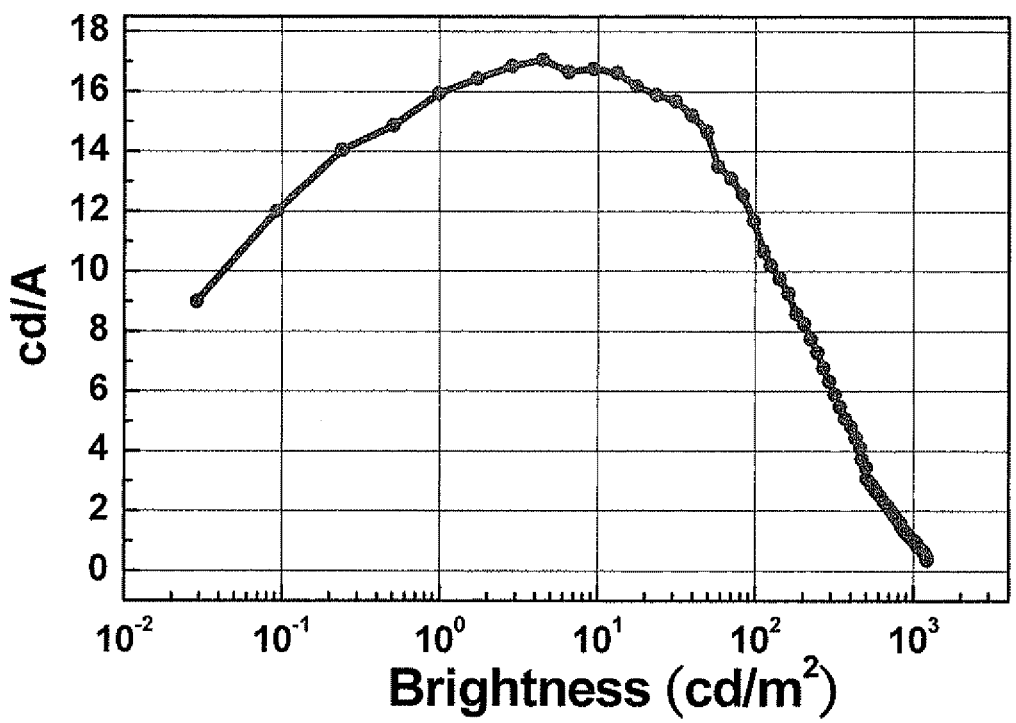

The current-voltage (I-V) characterization of the light-emitting devices was performed with a source-measurement unit (SMU) and a calibrated Si photodiode with Photo Research PR650. EL spectra of devices were collected by a calibrated CCD spectragraph. FIG. 6 shows the structure of the blue OLED fabricated employing Ir complex (4) of the present invention and the structures of the compounds used together with an energy level diagram. The performance of the blue OLEDs fabricated in this example are shown in FIG. 7 and Table 2.

TABLE 2

| Device | | External Quantum Efficiency (%) | Luminance Efficiency (cd/A) | Power Efficiency (lm/W) |
|---|---|---|---|---|
| Blue OLED | Peak | 10.13 | 17.06 | 10.43 |
| | 100 cd/m$^2$ | 6.80 | 11.69 | 4.71 |

A white OLED device structure and materials used were ITO/α-NPD (30 nm)/TCTA (20 nm)/CzSi: (4) 8.0 wt. % (15 nm)/UGH2: (13) 8.0 wt. % (5 nm)/BCP (45 nm)/Cs$_2$CO$_3$ (2 nm)/Al (150 nm). The α-naphthylphenylbiphenyl diamine (α-NPD) and 4,4',4"-tri(N-carbazolyl)triphenylamine (TCTA) were used as the hole-transport layer (HTL). Double emitting layers (CzSi doped with 8.0 wt. % of (4), UGH2 doped with 8.0 wt. % of (13)) were used to achieve better balance between hole and electron injection/transport and thus to move the exciton formation zone away from the quenching interfaces with carrier-transport layers, taking advantage of the hole-transport nature of CzSi and the electron-transport nature of UGH2. Finally, 2,9-dimethyl-4,7-diphenyl-1,10-phenanthroline (BCP) was used as the electron-transport layer, and Al or Cs$_2$CO$_3$ were used as the electron-injection layer.

Figure 8:
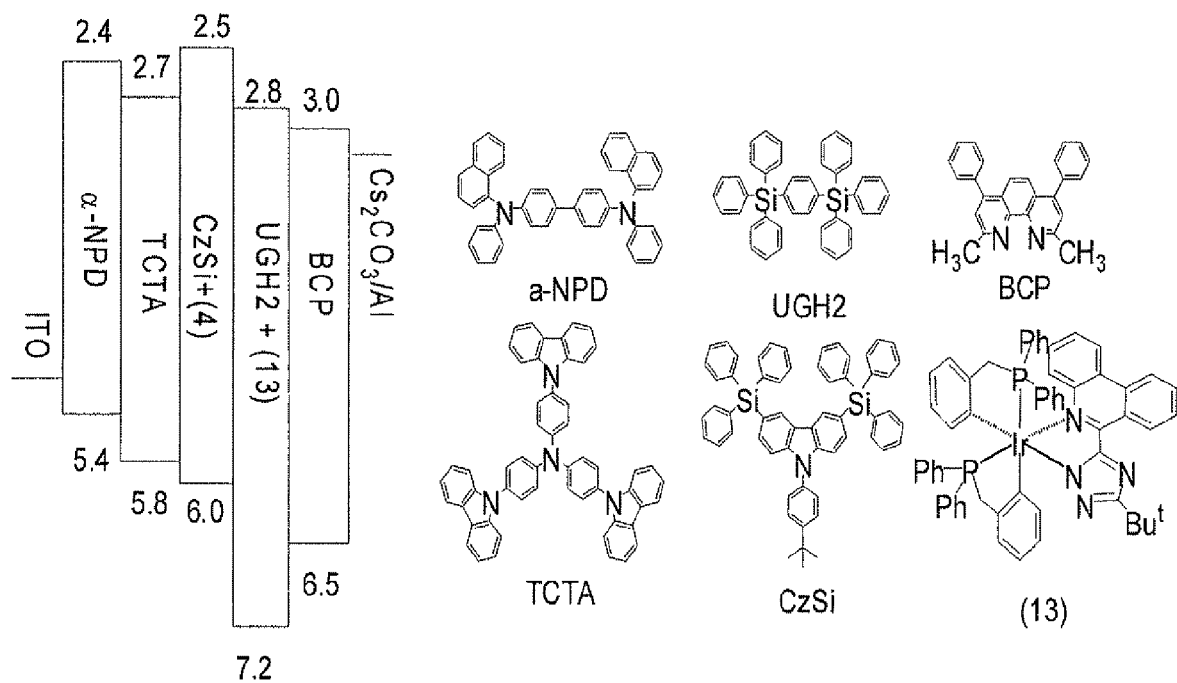
FIG. 8 shows the structural drawing of the white OLED fabricated employing Ir complexes (4) and (13) and the structures of the compounds used together with an energy level diagram.
Figure 9A:
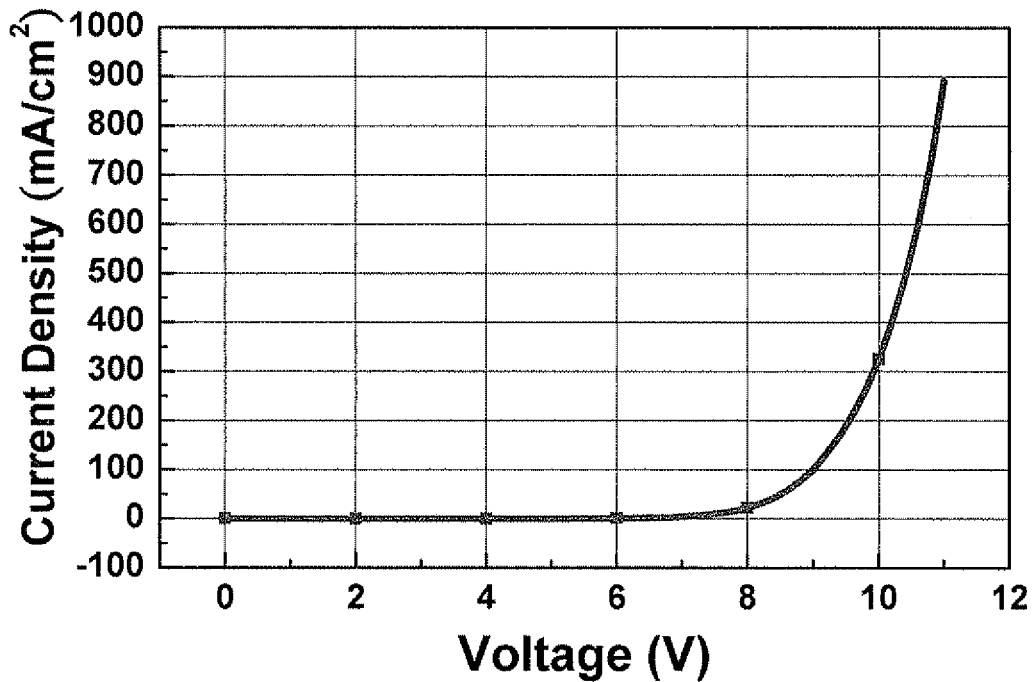
FIG. 9 shows the performance data of the white OLED fabricated employing Ir complexes (4) and (13) as phosphor. (a) plot of current density versus driving voltage, (b) plot of external quantum efficiency versus brightness, (c) plot of power efficiency versus brightness, and (d) plot of luminescent efficiency versus brightness
Figure 9B:
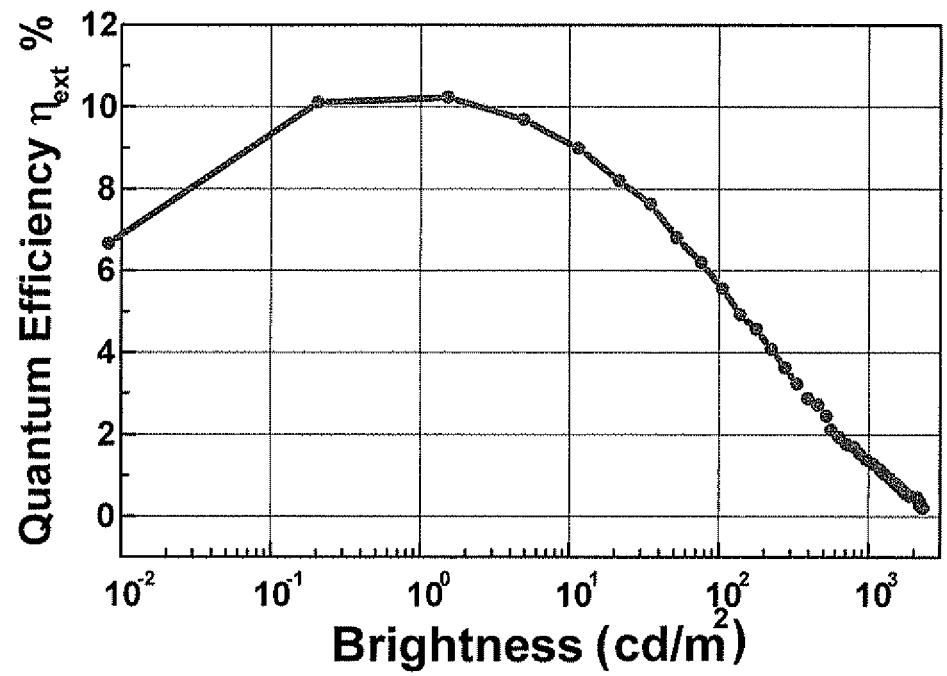
Figure 9C:
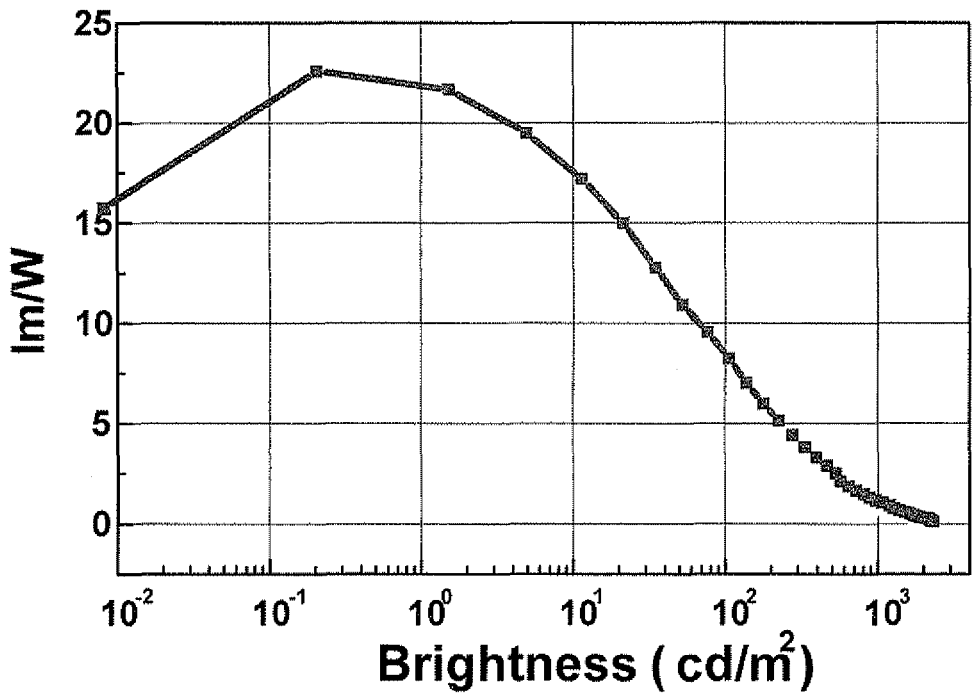
Figure 9D:
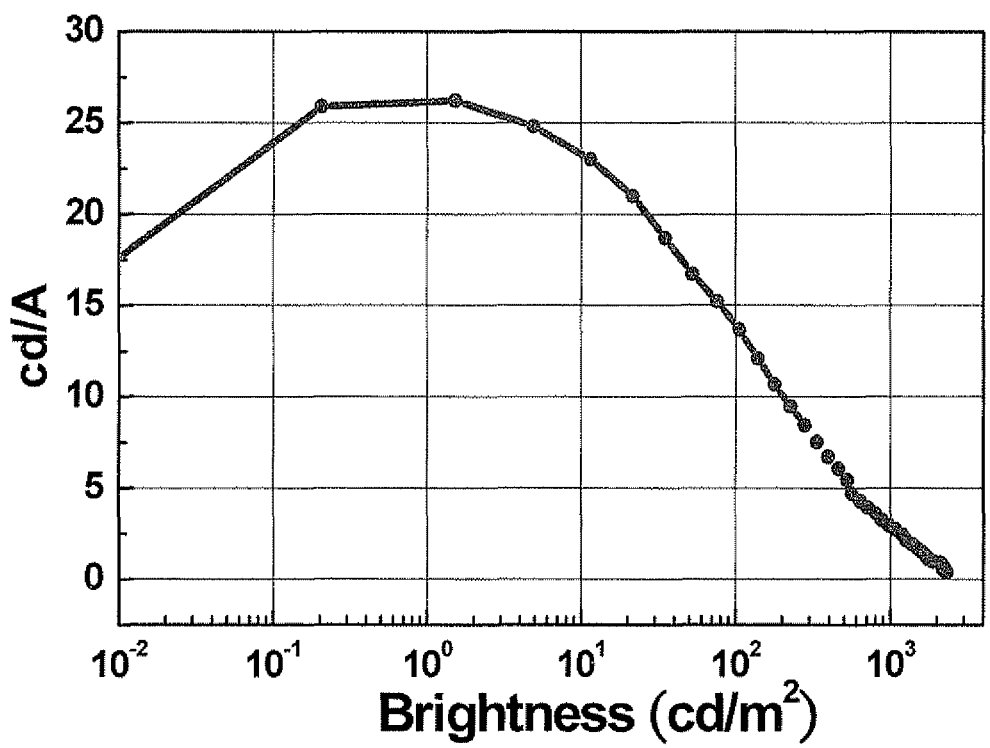

The current-voltage (I-V) characterization of the light-emitting devices was performed with a source-measurement unit (SMU) and a calibrated Si photodiode with Photo Research PR650. EL spectra of devices were collected by a calibrated CCD spectragraph. FIG. 8 shows the structure of the white OLED fabricated employing Ir complexes (4) and (13) and the structures of the compounds used together with an energy level diagram. The performance of the white OLED fabricated employing 4 and 13 are shown in FIG. 9 and Table 3

TABLE 3

| Device | | External Quantum Efficiency (%) | Luminance Efficiency (cd/A) | Power Efficiency (lm/W) |
|---|---|---|---|---|
| white OLED | Peak | 10.93 | 28.70 | 24.70 |
| | 100 cd/m$^2$ | 7.20 | 18.22 | 10.60 |

The invention claimed is:

1. A phosphorescent transition metal complex represented by formulas Ia, Ib, Ic, or their stereo isomers, which comprises one facially arranged, carbon-phosphorus-carbon (C^P^C) tridentate chelate, and one bidentate carbon-nitrogen (C^N) or azolate-nitrogen (A^N) anionic chromophoric chelate, and one arbitrary neutral donor ligand (L); or comprises one facially arranged, carbon-phosphorus-carbon (C^P^C) tridentate chelate, and one neutral diimine nitrogen-nitrogen (N^N) chromophoric chelate, and one arbitrary anionic donor ligand (X):

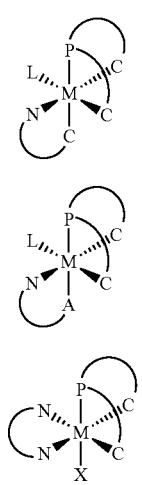

wherein M is iridium, osmium or ruthenium;

the C^N, A^N or N^N chelates have a general representation of $Ar^1$-$Ar^2$, wherein $Ar^1$ is aryl, substituted aryl or polyaromatic fragment in the C^N chelate; pyrrolide, functionalized pyrrolide, pyrazolate, functionalized pyrazolate, triazolate, functionalized triazolate or tetrazolate group in the A^N chelate; or heterocyclic nitrogen donor group in the diimine N^N chelate, while $Ar^2$ in each of the C^N, A^N and N^N chelates of formula Ia, Ib and Ic is a neutral heteroaromatic N-containing donor group; and the C^P^C chelate has a formula of $PR^4(OAr^5)_2$, wherein $R^4$ is alkyl, aryl, substituted aryl, aryloxyl, or substituted aryloxyl; and $Ar^5$ is an aryl or substituted aryl comprising a $R^5$ substituent, wherein $R^5$ is alkyl, alkoxyl, halide, or pseduohalide; and a carbon atom in each $Ar^5$ is ortho cyclometalated to M.

2. The complex of claim 1, wherein the carbon-nitrogen (C^N) chelate is

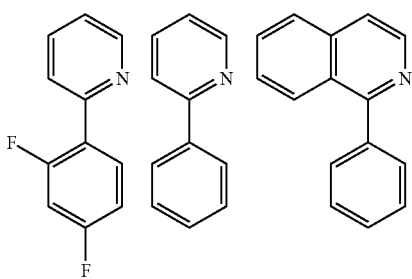

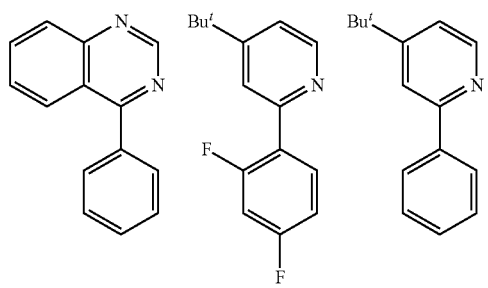

wherein $Bu^t$ is tert-butyl.

3. The complex of claim 1, wherein the azolate-nitrogen (A^N) chelate is

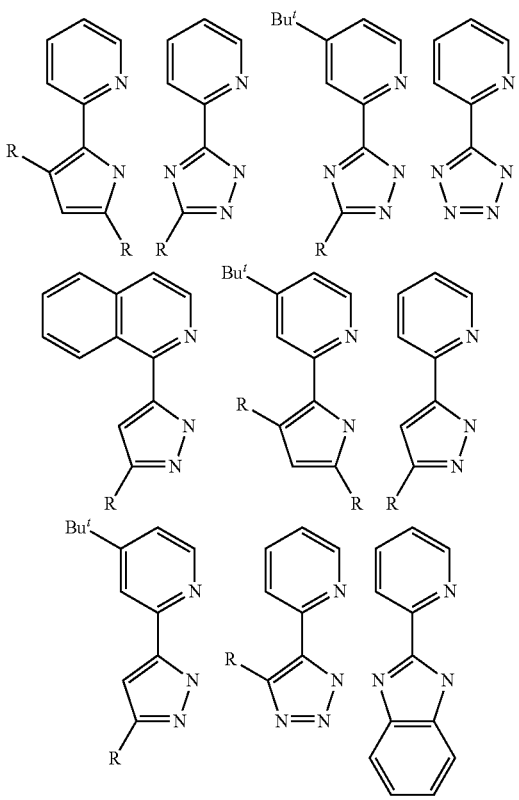

wherein R is hydrogen, $CF_3$, methyl, tort-butyl, small alkyl, phenyl or substituted phenyl group, and $Bu^t$ is tort-butyl.

4. The complex of claim 1, wherein the diimine nitrogen-nitrogen (N^N) chelate is

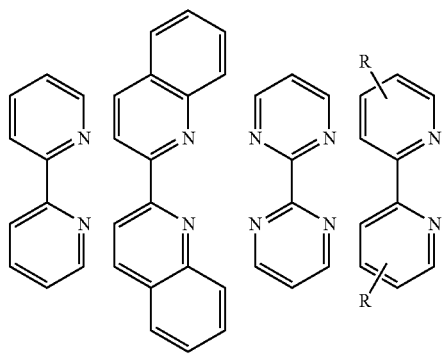

wherein R is hydrogen, methyl, tert-butyl, small alkyl, phenyl, substituted aryl, fluoride, halide, pseudohalide, methoxyl, dimethylamino, or diphenylamino.

5. The complex of claim 1, wherein the diimine nitrogen-nitrogen (N^N) chelate is

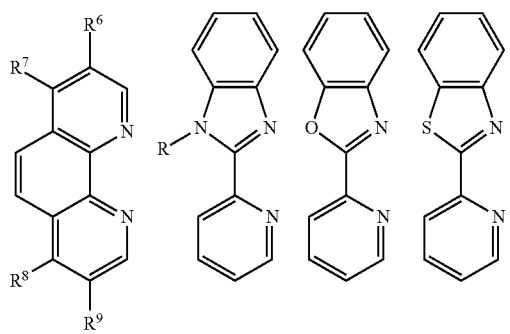

wherein R, $R^6$, $R^7$, $R^8$, and $R^9$ independently are hydrogen, methyl, ethyl, small alkyl, phenyl, or substituted phenyl.

6. The complex of claim 1 represented by the following formula:

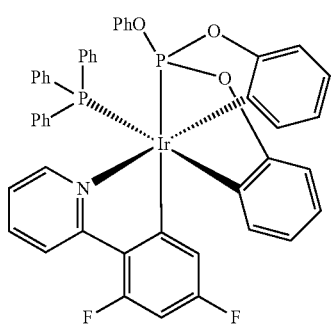

wherein Ph is phenyl.

7. The complex of claim 1 represented by the following formula:

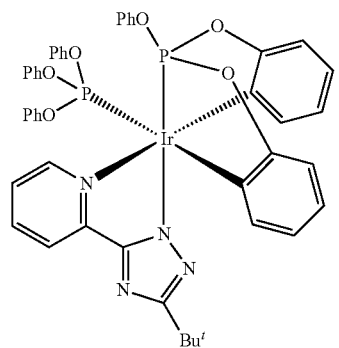

wherein Ph is phenyl, and $Bu^t$ is tert-butyl.

8. The complex of claim 1 represented by the following formula:

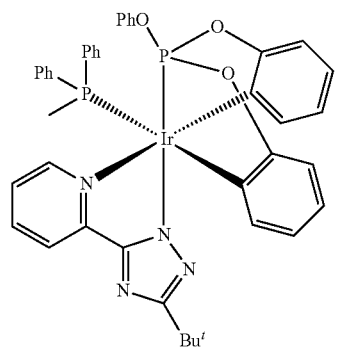

wherein Ph is phenyl, and $Bu^t$ is tert-butyl.

9. The complex of claim 1 represented by the following formula:

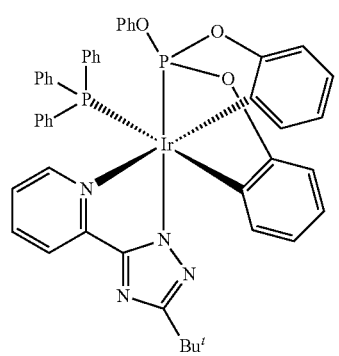

wherein Ph is phenyl, and $Bu^t$ is tert-butyl.

10. The complex of claim 1 represented by the following formula:

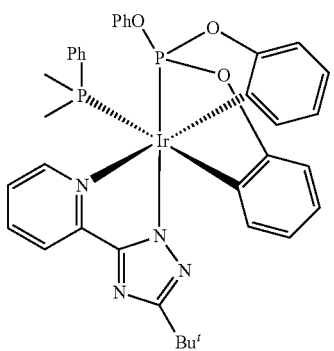

wherein Ph is phenyl, and Bu$^t$ is tert-butyl.

11. The complex of claim 1 represented by the following formula:

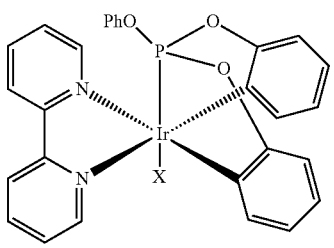

wherein Ph is phenyl, and X=chloride and thiocyanate.

12. The complex of claim 1 represented by the following formula:

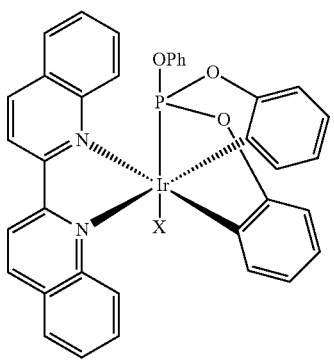

wherein Ph is phenyl and X=chloride and thiocyanate.

13. The complex of claim 1, wherein M is iridium, and Ar$^5$ is phenyl or substituted phenyl.

14. The complex of claim 13, wherein the complex is presented by the formula Ic, wherein X in formula Ic is an inorganic anion selected from the group consisting of acetate, halide, cyanide, isocyanate, thiocyanate, and pseudohalide; or an organic anion selected from the group consisting of aryl, alkoxyl, phenoxide, substituted phenoxide, azolate, thiolate, functionalized azolate, acetylide, and substituted acetylide.

15. The complex of claim 13, wherein the complex is presented by the formulas Ia or Ib, wherein L in formula Ia and Ib is phosphorous donor PR$^1$R$^2$R$^3$, and R$^1$, R$^2$, and R$^3$ independently are alkyl, alkoxyl, aryl, substituted aryl, aryloxyl or substituted aryloxyl.

16. The complex of claim 15, wherein R$^1$, R$^2$, and R$^3$ independently are methyl, phenyl, or phenoxyl.

17. The complex of claim 13, wherein the complex is presented by the formulas Ia or Ib, wherein L in formula Ia and Ib is a non-phosphorous donor ligand.

18. The complex of claim 17, wherein the non-phosphorous donor ligand is AsR$^1$R$^2$R$^3$, and R$^1$, R$^2$, and R$^3$ independently are alkyl, alkoxyl, aryl, substituted aryl, aryloxyl or substituted aryloxyl; and the arbitrary nitrogen donor ligand is pyridine or functionalized pyridine.

19. The complex of claim 13, wherein R$^4$ is methoxyl, phenoxyl, or phenyl.

20. The complex of claim 19, wherein R$^4$ is phenoxyl.

21. An organic light emitting diode, which comprises: a positive electrode formed on a substrate; a negative electrode; and a light emitting layer disposed between said positive electrode and said negative electrode, wherein said light emitting layer comprises a complex as set forth in claim 1 as an electrophosphorescent material.

22. The light-emitting diode of claim 21, wherein the metal is iridium, and Ar$^5$ is phenyl or substituted phenyl.

23. The light-emitting diode of claim 22, wherein R$^4$ is methoxyl, phenyl or phenoxyl.

24. The light-emitting diode of claim 22, wherein the complex is presented by the formula Ic, wherein X in formula Ic is an inorganic anion selected from the group consisting of acetate, halide, cyanide, isocyanate, thiocyanate, and pseudohalide; or an organic anion selected from the group consisting of aryl, alkoxyl, phenoxide, substituted phenoxide, azolate, thiolate, functionalized azolate, acetylide, and substituted acetylide.

25. The light-emitting diode of claim 22, wherein the complex is presented by the formulas Ia or Ib, wherein L is PR$^1$R$^2$R$^3$, and R$^1$, R$^2$, and R$^3$ independently are alkyl, alkoxyl, aryl, substituted aryl, phenoxide, or substituted phenoxide.

26. The light-emitting diode of claim 25, wherein R$^1$, R$^2$, and R$^3$ independently are methyl, phenyl, or phenoxyl.

27. A phosphorescent transition metal complex represented by formulas Ia, Ib, Ic, or their stereo isomers, which comprises one facially arranged, carbon-phosphorus-carbon (C^P^C) tridentate chelate, one bidentate carbon-nitrogen (C^N) or azolate-nitrogen (A^N) anionic chromophoric chelate, together with and one arbitrary neutral donor ligand (L); or comprises one facially arranged, carbon-phosphorus-carbon (C^P^C) tridentate chelate, and one neutral diimine nitrogen-nitrogen (N^N) chromophoric chelate, together with one arbitrary anionic donor ligand (X):

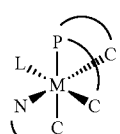

Ia

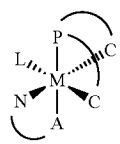

Ib

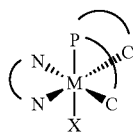

Ic wherein M is iridium, osmium or ruthenium;
the C^N, A^N, or N^N chelate have a general representation of $Ar^1$-$Ar^2$, wherein $Ar^1$ is aryl, substituted aryl or polyaromatic fragment in the C^N chelate; pyrrolide, functionalized pyrrolide, pyrazolate, functionalized pyrazolate, triazolate, functionalized triazolate or tetrazolate group in the A^N chelate; or heterocyclic nitrogen donor group in the diimine N^N chelate, while $Ar^2$ in each of the C^N, A^N and N^N chelates is a neutral heteroaromatic N-containing donor group; and (C^P^C) have a formula of $PR^4(CH_2Ar^5)_2$, wherein $R^4$ is alkyl, aryl, substituted aryl, aryloxyl, or substituted aryloxyl; and $Ar^5$ is an aryl or substituted aryl comprising a $R^5$ substituent, wherein $R^5$ is alkyl, alkoxyl, halide, or pseduohalide; and the two carbon atoms in the C^P^C tridentate chelate of the formulas represent the ortho-cyclometalated carbon atoms of the aryl rings, $Ar^5$.

* * * * *